United States Patent
Mohseni

(10) Patent No.: US 11,317,807 B2
(45) Date of Patent: May 3, 2022

(54) DETECTION OF FAST-NEURAL SIGNAL USING DEPTH-RESOLVED SPECTROSCOPY VIA INTENSITY MODULATED INTERFEROMETRY HAVING TUNABLE PUMP LASER

(71) Applicant: HI LLC, Los Angeles, CA (US)

(72) Inventor: Hooman Mohseni, Wilmette, IL (US)

(73) Assignee: HI LLC, Los Angeles, CA (US)

( * ) Notice: Subject to any disclaimer, the term of this patent is extended or adjusted under 35 U.S.C. 154(b) by 389 days.

(21) Appl. No.: 16/565,326

(22) Filed: Sep. 9, 2019

(65) Prior Publication Data

US 2020/0113439 A1 Apr. 16, 2020

Related U.S. Application Data

(60) Provisional application No. 62/781,098, filed on Dec. 18, 2018, provisional application No. 62/760,797, (Continued)

(51) Int. Cl.
*A61B 5/00* (2006.01)

(52) U.S. Cl.
CPC .......... *A61B 5/0042* (2013.01); *A61B 5/0075* (2013.01); *A61B 5/7282* (2013.01); (Continued)

(58) Field of Classification Search
CPC ... A61B 5/0042; A61B 5/0075; A61B 5/7282; A61B 5/4064; A61B 2562/0238; (Continued)

(56) References Cited

U.S. PATENT DOCUMENTS 5,553,614 A * 9/1996 Chance ................ A61B 5/1455
600/407
5,564,417 A * 10/1996 Chance .............. A61B 5/14551
356/341
(Continued)

FOREIGN PATENT DOCUMENTS

EP 1589623 5/2008
WO WO-2010009452 A1 * 1/2010 ........... A61B 5/4064

OTHER PUBLICATIONS

"S. H. Yun, G. J. Tearney, J. F. de Boer, and B. E. Bouma, Pulsed-source and swept-source spectral-domain optical coherence tomography with reduced motion artifacts, Nov. 15, 2004, Opt Express, 12(23), 5614-5624" (Year: 2004).*
(Continued)

*Primary Examiner* — Serkan Akar
*Assistant Examiner* — James F McDonald
(74) *Attorney, Agent, or Firm* — Michael J. Bolan; Vista IP Law Group, LLP

(57) ABSTRACT

An optical measurement system and method are provided. Pump sample light and probe sample light are delivered through into an anatomical structure of a user. The anatomical structure has molecules having a resonant vibrational frequency equal to the difference between a first optical frequency of the pump sample light and a second optical frequency of the probe sample light, whereby a portion of the probe sample light is inelastically scattered by the molecules as signal light encoded with a physiological event occurring in the molecules, and whereby sample light comprising the signal light exits the anatomical structure. Signal light in the exiting sample light is detected, and an electrical signal representative of the signal light is outputted. The electrical signal is analyzed, and based on this analysis, the
(Continued)

presence and the depth of the physiological event in the anatomical structure is determined.

26 Claims, 25 Drawing Sheets

Related U.S. Application Data filed on Nov. 13, 2018, provisional application No. 62/745,939, filed on Oct. 15, 2018.

(52) U.S. Cl.
CPC ........... *A61B 5/0086* (2013.01); *A61B 5/4064* (2013.01); *A61B 2562/0238* (2013.01); *A61B 2576/026* (2013.01)

(58) Field of Classification Search
CPC ............ A61B 2576/026; A61B 5/0086; A61B 5/0059; A61B 5/0095; A61B 5/0097; A61B 5/0066; A61B 5/7285; A61B 5/0004; A61B 2090/3735; A61B 2090/3979; A61B 5/0035; A61B 5/0033; A61B 18/20; A61B 5/0073; A61B 2562/146; A61B 2018/20361; A61B 2562/0242; G06T 7/0012; G06T 7/0014; G06T 7/0016; G02B 30/00
See application file for complete search history.

(56) References Cited

U.S. PATENT DOCUMENTS

| | | | | |
|---|---|---|---|---|
| 8,553,219 | B2* | 10/2013 | Patil | G01J 3/453 356/301 |
| 9,008,142 | B2* | 4/2015 | Minneman | H01S 5/0652 372/50.1 |
| 9,464,883 | B2* | 10/2016 | Swanson | G01B 9/02051 |
| 9,510,758 | B2* | 12/2016 | Warger, II | A61B 3/14 |
| 2017/0135583 | A1* | 5/2017 | Blodgett | G03H 1/0005 |
| 2018/0289256 | A1* | 10/2018 | Murata | A61B 3/1225 |

OTHER PUBLICATIONS

"W Dement, N Kleitman, Cyclic variations in EEG during sleep and their relation to eye movements, body motility, and dreaming, Nov. 1957, Electroencephalography and Clinical Neurophysiology, vol. 9, Issue 4, 1957, 673-690" https://doi.org/10.1016/0013-4694(57)90088-3. (Year: 1957).*

"R. Dandliker, The concept of modes in optics and photonics, 2000, Sixth International Conference on Education and Training in Optics and Photonics, SPIE, vol. 3831 (2000)" (Year: 2000).*

"A. Dunn, H. Bolay, M. Moskowitz, and D. Boas, Dynamic Imaging of Cerebral Blood Flow Using Laser Speckle, Mar. 1, 2001, Journal of Cerebral Blood Flow & Metabolism, vol. 21 issue: 3, pp. 195-201" (Year: 2001).*

T Durduran, R Choe, W B Baker and A G Yodh, "Diffuse optics for tissue monitoring and tomography," IOP Publishing, Reports on Progress in Physics, Rep. Prog. Phys. 73 (2010) 076701, (43 pages).

Takura Ideguchi, Simon Holzner, Birgitta Bernhardt, Guy Guelachvili, Nathalie Picque & Theodor W. Hansch, "Coherent Raman spectro-imaging with laser frequency combs," Oct. 17, 2013 | vol. 502 | Nature 3 5 5, (8 pages).

Francisco E. Robles, Martin C. Fischer, and Warren S. Warren, "Dispersion-based stimulated Raman scattering spectroscopy, holography, and optical coherence tomography," Jan. 11, 2016 | vol. 24, No. 1 | DOI:10.1364/OE.24.000485 | Optics Express 485, (14 pages).

Vijitha Periyasamy, Sanchita Sil, Gagan Dhal, Freek Ariese, Siva Umapathy and Manojit Pramanike, "Experimentally validated Raman Monte Carlo simulation for a cuboid object to obtain Raman spectroscopic signatures for hidden material," J. Raman Spectrosc. 2015, 46, 669-676, (24 pages).

Mutsuo Nuriya, Jiang Jiang, Boaz Nemet, Kenneth B. Eisenthal, and Rafael Yuste, "Imaging membrane potential in dendritic spines," 786-790 PNAS Jan. 17, 2006 vol. 103 No. 3, (5 pages).

Darcy S. Peterka, Hiroto Takahashi, and Rafael Yuste, "Imaging Voltage in Neurons," Neuron 69, Jan. 13, 2011, (13 pages).

Hyeon Jeong Lee, Delong Zhang, Ying Jiang, Xiangbing Wu, Pei-Yu Shih, Chien-Sheng Liao, Brittani Bungart,|| Xiao-Ming Xu, Ryan Drenan, Edward Bartlett, and Ji-Xin Cheng, "Label-Free Vibrational Spectroscopic Imaging of Neuronal Membrane Potential," J. Phys. Chem. Lett. 2017, 8, 1932-1936, (5 pages).

Bin Liu, Hyeon Jeong Lee, Delong Zhang, Chien-Sheng Liao, Na Ji, Yuanqin Xia and Ji-Xin Cheng, "Label-free spectroscopic detection of membrane potential using stimulated Raman scattering," Applied Physics Letters 106, 173704 (2015), (6 pages).

Patrick Theer, Winfried Denk, Mordechai Sheves, Aaron Lewis, and Peter B. Detwiler, "Second-Harmonic Generation Imaging of Membrane Potential with Retinal Analogues," Biophysical Journal vol. 100 Jan. 2011 232-242, (11 pages).

Francisco E. Robles, Kevin C. Zhou, Martin C. Fischer, and Warren S. Warren, "Stimulated Raman scattering spectroscopic optical coherence tomography," vol. 4, No. 2 / Feb. 2017 / Optica, (4 pages).

Martha Z. Vardaki, Benjamin Gardner, Nicholas Stone and Pavel Matousek, "Studying the distribution of deep Raman spectroscopy signals using liquid tissue phantoms with varying optical properties," Analyst, 2015, 140, 5112-5119, (8 pages).

Ji-Xin Cheng and X. Sunney Xie, "Vibrational spectroscopic imaging of living systems: An emerging platform for biology and medicine," Science, Nov. 27, 2015 • vol. 350 Issue 6264 (11 pages).

Xueli Chen, Chi Zhang, Peng Lin, Kai-Chih Huang, Jimin Liang, Jie Tian, & Ji-Xin Cheng, "Volumetric chemical imaging by stimulated Raman projection microscopy and tomography," Nature Communications | 8:15117 | DOI:10.1038/ncomms15117, (12 pages).

Michael A. Choma, et al., "Sensitivity Advantage of Swept Source and Fourier Domain Optical Coherence Tomography," Optics Express, vol. 11, No. 18, Sep. 8, 2003, (7 pages).

Borycki, Dawid, et al., "Interferometric Near-Infrared Spectroscopy (iNIRS) for Determination of Optical and Dynamical Properties of Turbid Media," Optics Express, vol. 24, No. 1, Jan. 11, 2016, (26 pages).

Hill D.K. and Keynes, R.D., "Opacity Changes in Stimulated Nerve," J. Physiol., vol. 108, pp. 278-281 (1949), (4 pages).

Gratton G., Fabiani M, "Fast-neural Imaging of Human Brain Function," vol. 4, Article 52, pp. 1-9 (Jun. 2010), (9 pages).

Foust A.J. and Rector D.M., "Optically Teasing Apart Neural Swelling and Depolarization," Neuroscience, vol. 145, pp. 887-899 (2007), (21 pages).

\* cited by examiner

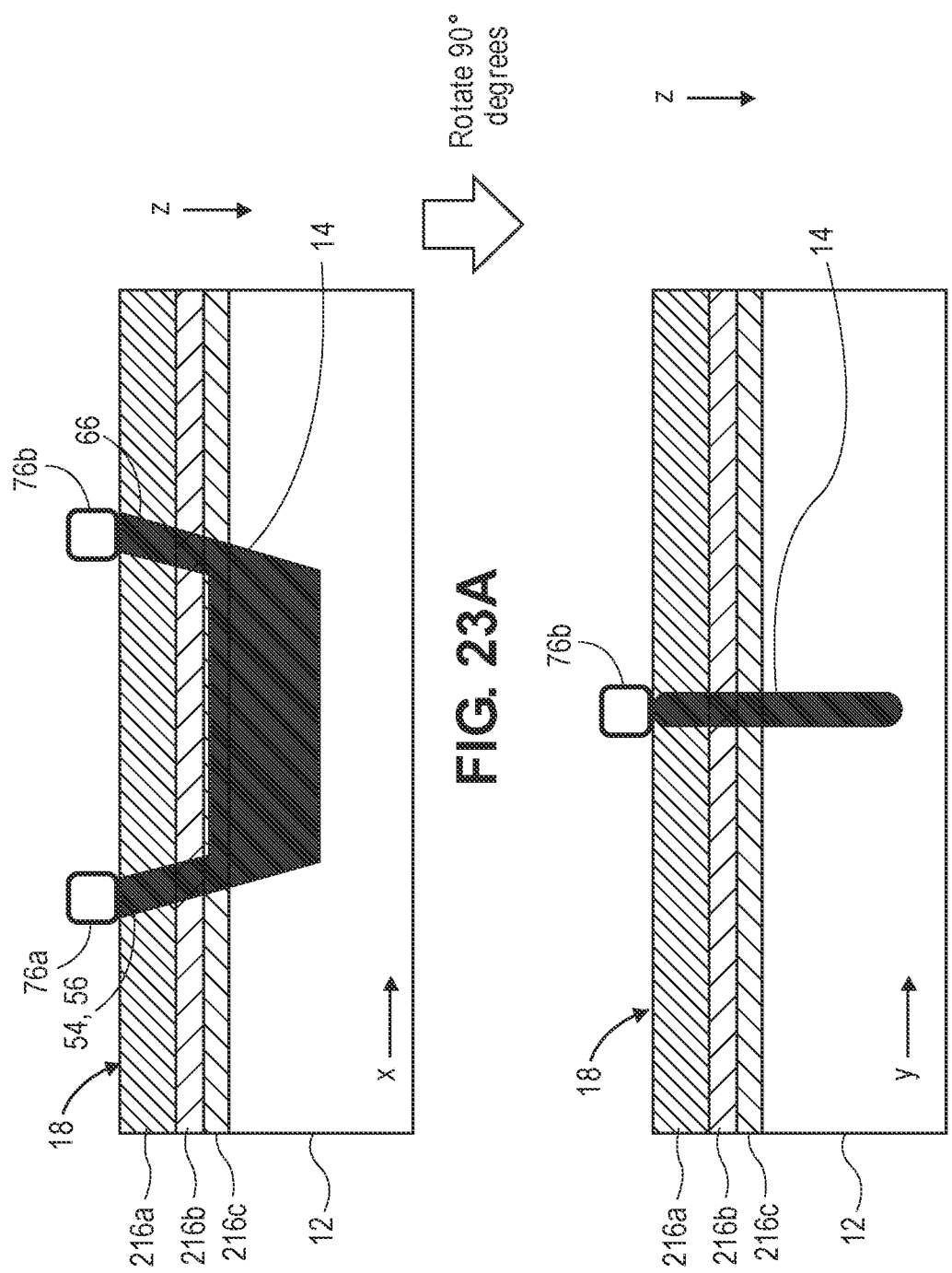

DETECTION OF FAST-NEURAL SIGNAL USING DEPTH-RESOLVED SPECTROSCOPY VIA INTENSITY MODULATED INTERFEROMETRY HAVING TUNABLE PUMP LASER

RELATED APPLICATION DATA

Pursuant to 35 U.S.C. § 119(e), this application claims the benefit of U.S. Provisional Patent Application Ser. No. 62/745,939, filed Oct. 15, 2018, U.S. Provisional Patent Application Ser. No. 62/760,797, filed Nov. 13, 2018, U.S. Provisional Patent Application Ser. No. 62/781,098, filed Dec. 18, 2018, which are all expressly incorporated herein by reference.

FIELD OF THE INVENTION

The present inventions relate to methods and systems for non-invasive measurements in the human body, and in particular, methods and systems related to detecting physiologically-dependent optical parameters in the human body.

BACKGROUND OF THE INVENTION

Measuring neural activity in the brain is useful for medical diagnostics, neuromodulation therapies, neuroengineering, or brain-computer interfacing. Conventional methods for measuring neural activity in the brain include diffusive optical measurement techniques, which employ moderate amounts of near-infrared or visible light radiation, thus being comparatively safe and gentle for a biological subject in comparison to X-Ray Computed Tomography (CT) scans, positron emission tomography (PET), or other methods that use higher-energy and potentially harmful ionizing radiation. Moreover, in contrast to methods, such as functional magnetic resonance imaging (fMRI), these optically-based measurement methods do not require large magnets or magnetic shielding, and thus, can be scaled to wearable or portable form factors, which is especially important in applications, such as brain-computer interfacing.

However, because optical measurement techniques rely on light, which scatters many times inside brain, skull, dura, pia, and skin tissues, the light paths occurring in these techniques comprise random or "diffusive" walks, and therefore, only limited spatial resolution can be obtained by a conventional optical detector, often on the order of centimeters, with usable penetration depths being limited to a few millimeters. The reason for this limited spatial resolution is that the paths of photons striking the detector in such schemes are highly variable and difficult, and even impossible, to predict without detailed microscopic knowledge of the scattering characteristics of the brain volume of interest, which is typically unavailable in practice (i.e., in the setting of non-invasive measurements through skull for brain imaging and brain interfacing). In summary, light scattering has presented challenges for optical measurement techniques in achieving high spatial resolution inside tissue regions at depths below a user's skull, e.g., multiple centimeters. Moreover, the diffusive nature of light propagation also creates challenges for measurements of fast changes in optical scattering inside tissue, since essentially all paths between source and detector are highly scattered to begin with.

One commercially available non-invasive optical imaging method, referred to as optical coherence tomography (OCT), is capable of acquiring images with high z-resolution (depth), but at relatively shallow depths (1 mm-2 mm). Traditional OCT systems use coherent light (typically light in the near-infrared spectrum) to capture sub-surface images within optical scattering media (such as biological tissue) at a micrometer-resolution. The OCT system directs an optical beam at biological tissue and collects a small portion of the light that reflects from sub-surface features of the biological tissue. Although most of the light directed at the biological tissue is not reflected, but rather, diffusively scatters and contributes to background that may obscure the image, traditional OCT utilizes a holographic (or interferometric) technique to select, via optical path selection, the photons that directly reflect off of the sub-surface features (i.e., the ballistic backscattered photons), and reject photons that scatter multiple times in the biological tissue before detection.

In particular, in a traditional OCT system, light from a light source is split into two paths along two different arms of an interferometer: a reference arm and a sample arm. In the sample arm, sample light is backscattered through a sample medium, and in the reference arm, reference light is back-reflected by a mirror where it recombines with the backscattered sample light at a coupler. Interference light is formed by any sample light that has an optical path length that matches, within the coherence length of the optical source, the optical path length traveled by the reference light. The intensity of the backscattering sample light having that optical path length can then be detected within the interference light.

Previous commercial OCT systems acquired data in the time domain (TD-OCT), and coherence gated the backscattered light from various depths in the biological tissue by adjusting the position of the mirror to tune the optical path length of the reference, such that only sample light having the matching optical path length is selected for detection at any given time. Current commercial OCT systems acquire data in the Fourier domain (FD-OCT), and do not involve adjusting the delay of the reference arm, but rather involve acquiring an interferometric signal as a function of optical wavelength by combining the sample light and the reference light from a source with a finite spectral width at a fixed reference arm delay, and then Fourier-transforming the spectral or frequency-resolved interference as a function of photon time-of-flight to obtain the various depths in the biological tissue. It has been shown that FD-OCT has a significantly greater signal-to-noise (SNR) than TD-OCT (see Michael A. Choma, et al., "*Sensitivity Advantage of Swept Source and Fourier Domain Optical Coherence Tomography*," Optics Express, Vol. 11, No. 18, 8 Sep. 2003). Two distinct methods have been developed that employ the FD approach: (1) swept-source (SS-OCT), which time-encodes optical wavelengths by rapidly tuning a narrowband source through a broad optical bandwidth; and 2) spectral domain (SD-OCT), which uses a broadband light source to achieve spectral discrimination.

Regardless of the type, the depth at which a traditional OCT system images biological tissue is limited, because at greater depths the proportion of light that escapes without scattering (i.e., the ballistic light) is too small to be detected. Thus, the clinical applications of a traditional OCT system have, thus far, been limited to imaging sub-surface features, such as obtaining high-resolution ophthalmic images of the retina. As such, traditional OCT systems are presently insufficient for measuring neural activity in the regions of the brain at deeper depths (i.e., deeper than 2 mm).

Another type of diffusive optical measurement technique, referred to as interferometric Near-Infrared Spectroscopy (iNIRS) (see Borycki, Dawid, et al., "*Interferometric Near-Infrared Spectroscopy (iNIRS) for Determination of Optical and Dynamical Properties of Turbid Media*," Optics Express, Vol. 24, No. 1, Jan. 11, 2016), has been developed. While traditional OCT utilizes low-coherence interferometry to produce cross-sectional images of biological specimens with a resolution of few micrometers and an imaging range of 1-2 mm, the goal of iNIRS is to use high coherence interferometry to measure optical and dynamical properties of thick scattering media at a depth on the order of a few centimeters, at the cost of reduced axial resolution.

As discussed in Borycki, iNIRS can be implemented in a time domain approach, referred to as TD NIRS, or a frequency domain approach, referred to as FD NIRS. In TD NIRS, a near-infrared picosecond light pulse is delivered into tissue, and the reflected optical intensity is detected and analyzed as a function of time. In particular, the optical properties (e.g., absorption and scattering coefficients) of the tissue can be determined from the temporal features, such as slope and the peak location, of the photon distribution of time-of-flight (DTOF) of the resulting temporal signal. In FD NIRS, sinusoidally modulated light is delivered into tissue. The optical properties of the tissue are determined from the amplitude attenuation and phase shift of the reflected optical light. However, FD NIRS typically does not directly resolve the DTOF, and the modulation/demodulation schemes can be complex and expensive. One embodiment of the FD NIRS system disclosed in Borycki utilizes a frequency-swept laser with an instantaneous linewidth and tuning range narrower by several orders of magnitude than in typical OCT systems, enabling the measurement of longer photon path lengths (up to tens of centimeters) at the cost of reduced axial resolution.

Nearly all diffusive optical measurement techniques to date offer relatively poor temporal resolution (100 ms-1 sec per sample), as they are primarily designed to detect hemodynamics that vary on a similarly slow time scale. There is an increasing interest in measuring fast-neural signals, which has been speculated to be caused by optical scattering that occur when light propagating through active neural tissue (e.g., active brain tissue) is perturbed through any one or more of a variety of mechanisms, including, but not limited to, cell swelling, cell volume change, changes in membrane potential, changes in membrane geometry, ion redistribution, birefringence changes, etc. (see Hill D. K. and Keynes, R. D., "Opacity Changes in Stimulated Nerve," J. Physiol., Vol. 108, pp. 278-281 (1949); Foust A. J. and Rector D. M., "Optically Teasing Apart Neural Swelling and Depolarization," Neuroscience, Vol. 145, pp. 887-899 (2007)). Because fast-neural signals are associated with neuronal activity, rather than hemodynamic responses, fast-neural signals may be used to detect brain activity with relatively high temporal resolution. However, to the extent that iNIRS systems can measure fast-neural signals, the mechanisms that cause fast-neural signals to appear in such measurements are currently not well known.

As discussed in Gratton G., Fabiani M, "Fast-neural Imaging of Human Brain Function," Vol. 4, Article 52, pp. 1-9 (June 2010)), the basic assumption for detecting naturally occurring fast-neural signals is that fast-neural signals change the path length distribution of light propagating through a sample. The mechanisms of fast-neural signals alter the amount or directionality distribution of local scattering, thereby scattering light towards deeper or shallower depths, resulting in more or less time spent in the tissue or other changes in the fraction of photons traveling on deep versus shallower paths through tissue, or more generally longer or shorter paths through tissue. Thus, fast-neural signals give rise to or are correlated with a change in average optical path length between source and for diffusive light propagating through the sample.

Gratton concludes that phase delay measurements are particularly interesting for detecting fast-neural signals associated with changing light scattering inside the brain since, compared to light intensity measurements (as performed by the FD NIRS technique), since phase delay measurements have a greater sensitivity for deeper locations due to the fact that photons traveling a very long path have a greater influence on the mean value of phase delay; phase delay measurements have a greater spatial resolution due to the large effect on the phase value in response to even small changes in the relative number of photons traveling long or short paths (5-10 mm for phase delay measurement compared to 10-20 mm for intensity measurements); and phase delay measurements are largely insensitive to variations in the total amount of light injected into the tissue or measured by the detector, since such variations will equally influence photons traveling long and shorter paths, and therefore have no net effect on the phase delay parameter, and thus are largely insensitive to movements.

However, fast-neural signals are very small (on the order of $\frac{1}{1000}$ for intensity measurements and picoseconds or fractions thereof for phase delay measurement), and thus, there is a challenge separating fast-neural signals from background noise. Gratton has proposed reducing the background noise by using signal averaging over a large number of trials. The disadvantage of this is, of course, the requirement that multiple measurements would need to be taken to detect a fast-neural signal, limiting applicability for "real time" applications, e.g., brain-computer interfacing.

Another potential issue with regard to measuring fast-neural signals using conventional iNIRS systems is that longer wavelengths of light, as compared to the light needed to detect hemodynamic changes, may be needed to detect fast-neural signals. However, the light absorption of brain tissue at such longer wavelengths may limit the penetration depth of such light, thereby limiting the depth at which fast-neural signals may be detected in brain tissue. Furthermore, new laser sources and detectors may need to be developed to enable optical measurements at these longer wavelengths, thereby increasing the cost of such optical measurement systems.

Another issue with regard to known diffusive optical measurement techniques is, due to the diffusive nature of the light traveling between the optical source and optical detector, a relatively large banana-shaped optical path is created therebetween, limiting the lateral resolution of such techniques. To address this issue, such diffusive optical measurement techniques may employ a multitude of optical sources and detectors along the surface of the head to create many banana-shaped optical paths that can then be post-processed to laterally localize neural activity within the brain. However, such post-processing is time-consuming, and therefore, ultimately degrades the temporal resolution of such optical measurement techniques, limiting the applicability of "real time" instantaneous applications, e.g., brain-computer interfacing.

Therefore, there remains a need to provide a simpler and less expensive optical measurement system with an improved and reliable temporal and spatial sensitivity, depth penetration, and lateral spatial resolution, to measure fast-neural signals.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 23A is one profile view of one arrangement of the output port and input port of the wearable unit of FIG. 22, particularly illustrating the creation of a sample path in a user's head between the ports; and FIG. 23B is another profile view of the arrangement of the output port and input port of the wearable unit of FIG. 22.

DETAILED DESCRIPTION OF THE EMBODIMENTS

Figure 1:
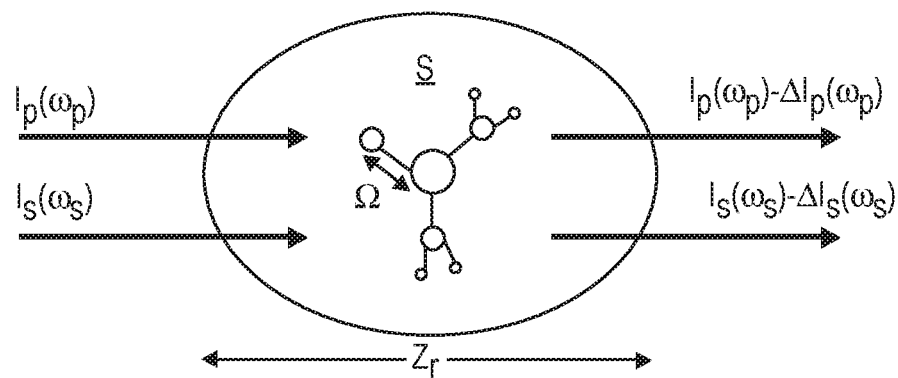
FIG. 1 is a plan view illustrating a stimulated Raman spectroscopy (SRS) technique for generating a Raman signal.

The embodiments of the optical measurement systems described herein are swept-source holographic optical systems (i.e., systems that mix detected signal light against reference light in order to increase the signal-to-noise ratio (SNR) of the relevant signal) similar to Near-Infrared Spectroscopy (iNIRS) systems. As such, the optical measurement systems described herein focus on the measurement of multiple-scattered signal light of different depth-correlated optical path lengths, as opposed to ballistic or single-scattered signal light measured by a conventional Optical Coherence Tomography (OCT) system or a swept-source OCT (SS-OCT) system, and therefore, are capable of detecting physiological events in tissue at a penetration depth of multiple centimeters.

Unlike conventional iNIRS systems, the optical measurement systems described herein are capable of robustly detecting fast-neural signals by performing Stimulated Raman Spectroscopy (SRS) to acquire a chemical signature of molecules, and in the embodiments illustrated below, the proteins in the membranes of neurons, and monitoring a change in this chemical signature in response to physiological events within the molecules, e.g., a fast-neural signal. Instead of encoding the presence and depth of a physiological event (e.g., a hemodynamic signal) within light that has undergone elastic scattering (Rayleigh scattering) within the anatomical structure, as is accomplished in conventional iNIRS systems, the optical measurement systems described herein ignore elastic scattering of the light, and in fact treat such elastic light scattering as background noise, and instead encodes the presence and depth of a physiological event (e.g., a fast-neural signal) within the light that has undergone inelastic scattering (Raman scattering) within the anatomical structure. The inelastic scattering of the light, i.e., the Raman signal, provides a chemical signature that reliably and robustly facilitates detection of physiological events, and in this case fast-neural signals. In other words, the optical measurement systems focus measurements on the changes in the molecules where fast-neural signals are known to occur (i.e., the neural membranes) exclusive of other molecules in the brain.

It is noted that although SRS has been performed on a limited basis on tissue (e.g., analyzing a thin layer of cells under a microscope), it was not known that SRS could be used to analyze three-dimensional anatomical structures, such as a brain, since the common understanding was that the nonlinear nature of SRS requires a very large photon flux, which could only be achieved in focused spots, and improved by short (pico-second) lasers. However, the inventor's evaluations show that non-invasive measurement of Raman signal is possible, since: a) the diffusive nature of the tissue, combined with its low loss at certain wavelength ranges (i.e., transparent spectral windows), produces photon densities that are much higher than a non-diffusive case (factor of ~7, depending on the tissue); and b) the number of cells that simultaneously fire in certain regions of the brain can be very large. For example, almost all Magnetoencephography (MEG) signals are predicted to be from simultaneous firing of ~10,000 neurons within a small millimeter-scale zone. It is known that MEG signals can be extremely useful for a brain-machine interface, and hence the ability to measure simultaneous firing of a large number of neurons optically is also extremely useful. Compared to the reported measurements of one neuron with conventional SRS, the SRS technique described herein allows measurement of synchronized firing of a large number of neurons to enhance the signal by 4 to 5 orders of magnitude. Furthermore, in known SRS methods, the change of intensity of the probe (and pump) beam(s) (described in further detail below) produced by the SRS process is measured directly. To achieve shot-noise limited measurement (i.e., the quantum limit of sensing), known SRS methods require that the probe light reaching the photodetectors be highly intensive. The SRS technique described herein uses interferometric approach to achieve shot-noise limited sensing for any intensity of light. It can be appreciated from the foregoing that there is a crucial difference when an SRS technique is applied to fully intact organs, such as the brain, as the amount of the transmitted light through such thick tissue is extremely small.

In SRS, a pump laser beam at an optical frequency $\omega_p$ and a probe laser beam at an optical frequency $\omega_s$ may coincide with a sample S, as illustrated in FIG. 1. When the optical frequency difference $\Delta\omega = \omega_p - \omega_s$ (also called the Raman shift) matches a particular molecular vibrational frequency $\Omega$ of the sample S, the molecules in the sample are coherently excited, and the incident pump laser beam photons are converted to probe laser beam photons, changing both the amplitude and phase of the initial pump and probe laser fields. As such, the intensity of the pump laser beam $I_p$ decreases, and the intensity of the probe laser beam $I_s$ increases. In effect, the sample S inelastically scatters the probe laser beam, thereby creating the difference in the probe laser beam $\Delta I_s$ (i.e., the Raman signal), which can be used to detect the spectral signature, and hence the molecular makeup, of the sample S.

Figure 2:
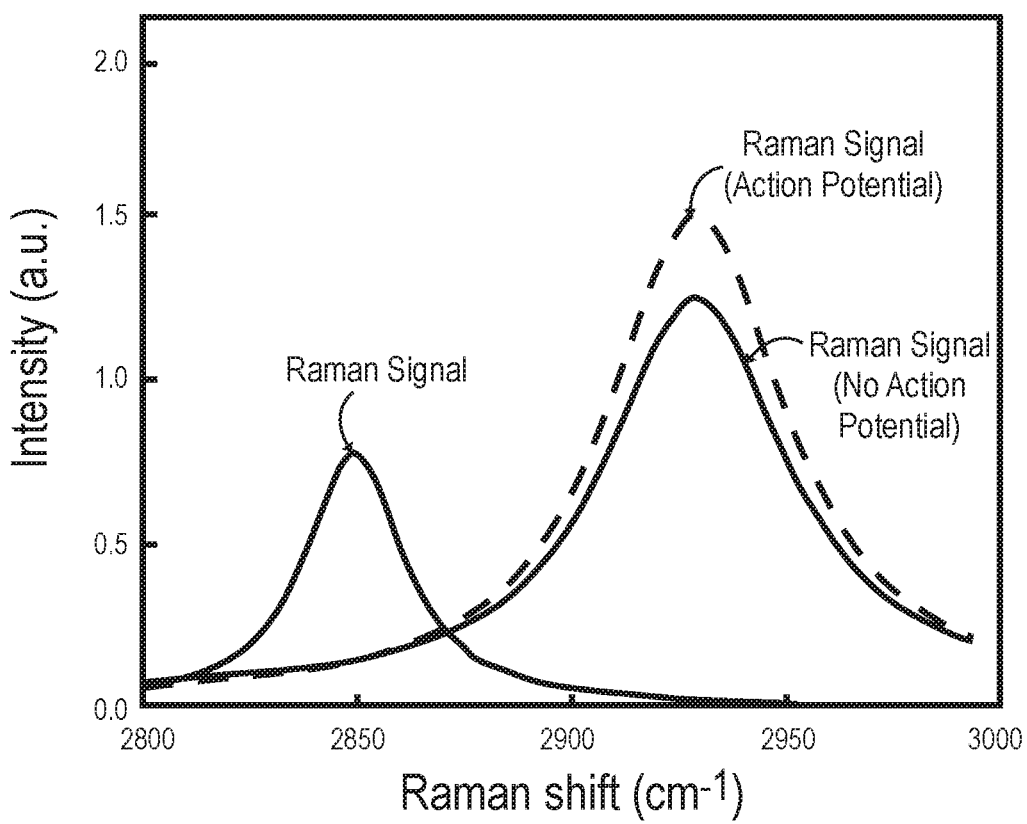
FIG. 2 is a plot illustrating Raman bands of a cell.

For example, it has been demonstrated that an exemplary Raman signal in the high wavenumber C—H stretching region (2800-3000 cm$^{-1}$) can be generated in neurons using a pulsed pump beam at 800 nm and a pulsed probe beam centered at 1040 nm (see Hyeon, Jeong Lee, et al., "Label-Free Vibrational Spectroscopic Imaging of Neuronal Membrane Potential," J. Phys. Chem. Lett. 2017, vol. 8., pp. 1932-1936 (April 2017), and Bin Liu, et al., "Label-Free Spectroscopic Detection of Membrane Potential Using Stimulated Raman Scattering," Applied Physics Letter, Vol. 106, 173704 (April 2015). As shown in FIG. 2, a distinctive Raman band centered at approximately 2850 cm$^{-1}$ (i.e., a vibration frequency of 85.5 THz) largely contributed by the CH$_2$ groups in acyl chains in lipids, and a distinctive Raman band centered at approximately 2930 cm$^{-1}$ (i.e., a vibration frequency of 88 THz), largely contributed by CH$_3$ groups in membrane proteins, appears in the high wavenumber C—H stretching region.

It has also been demonstrated that, despite the fact that the cell membrane may constitute perhaps 10$^{-3}$ of the volume of the cellular volume, the massive change of electric field across the cell membrane (10 to 100 Megavolt/meter) significantly changes the mechanical vibration properties of the molecular makeup of the cell membrane, particularly at 2930 cm$^{-1}$. As such, Raman signal at 2930 cm$^{-1}$ substantially increases (approximately 10%) in response to hyperpolarizing the neurons (i.e., in the presence of an action potential), as illustrated in FIG. 2, thereby revealing that the Raman signal at 2930 cm$^{-1}$ constitutes a vibrational signature of neural membrane potential (see Hyeon, Jeong Lee, et al., "Label-Free Vibrational Spectroscopic Imaging of Neuronal Membrane Potential," J. Phys. Chem. Lett. 2017, vol. 8., pp. 1932-1936 (April 2017). Thus, SRS is fully capable of robustly measuring neural activity, with a response time as fast as the neural action potential itself.

It should also be appreciated that the Raman signal $\Delta I_s$ is dependent upon the intensity of the pump laser beam $I_p$, and thus, will change in accordance with the pump laser beam $I_p$, as such:

$$\Delta I_s \approx I_s \cdot I_p \cdot N \cdot \varepsilon_{Raman}, \qquad [1]$$

where N is the number of molecules, and $\varepsilon_{Raman}$ is the Raman scattering cross section. Because the pump laser beam intensity $I_p$ will change the refractive index of the sample, the probe laser beam will also experience this change in the refractive index. Thus, the Raman signal can also be expressed as the complex change in the molecular refractive index of the sample S that is produced by the Raman process (observed by the change in amplitude and phase of the laser probe field $E_s(\omega_s)$, as follows:

$$E_s(\omega_s) = E_0(\omega_s) e^{-i\tilde{n}(w_s)\frac{2\omega z_r}{c}}, \qquad [2]$$

where $\tilde{n}(\omega_s)$ is the refractive index given by:

$$\tilde{n}(\omega_s) = \frac{3}{4n^2 \varepsilon c} \chi^{(3)}(\omega_p - \omega_s) I_p, \qquad [3]$$

$E_0$ is the initial probe laser field prior to interacting with the sample S, $\chi^{(3)}$ is the third-order nonlinear optical susceptibility of the sample S, $z_r$ is the interaction length, and c is the speed of light.

Although the basis of SRS is well understood, the application of SRS to iNIRS is not known. The optical measurement systems described herein use coherence detection, similar to iNIRS, to precisely measure the change of the refractive index generated during the SRS process, and as a function of the time-of-flight (TOF) of the photons in the probe laser beam. Therefore, the optical measurement systems described herein are not only chemically sensitive, but also have depth resolution. The optical measurement systems described herein are naturally robust and filter unwanted background optical signals (e.g., second harmonic generation). Furthermore, in contrast, unlike conventional pulsed wave (PW) SRS, which utilizes relatively expensive PW laser sources and is much more sensitive than continuous wave (CW) SRS, the optical measurement systems described herein may utilize less expensive continuous wave (CW) laser sources, while still providing performance and sensitivity commensurate with conventional, but more expensive, PW SRS systems.

The optical measurement systems described herein amplify the Raman signal by delivering a pump laser beam and a probe laser beam into the sample. The frequency of the Raman signal (the difference in optical frequencies between the pump laser beam and probe laser beam) is selected to excite vibrations of a specific chemical bond, and in this case the proteins in neural membranes, thereby amplifying the Raman signal. The pumped laser beam is intensity modulated to encode the Raman signal into the sample light that exits the anatomical structure. The probe laser beam is frequency swept to provide depth resolution of the Raman signal, with the range of such frequency sweep being narrower than the bandwidth of the Raman signal so as not to interfere with the Raman spectroscopy (i.e., such that the Raman signal does not significantly degrade across the frequency sweep). The optical measurement systems described herein utilize interferometry to path-length select (depth resolution) the intensity modulated Raman signal.

Figure 3:
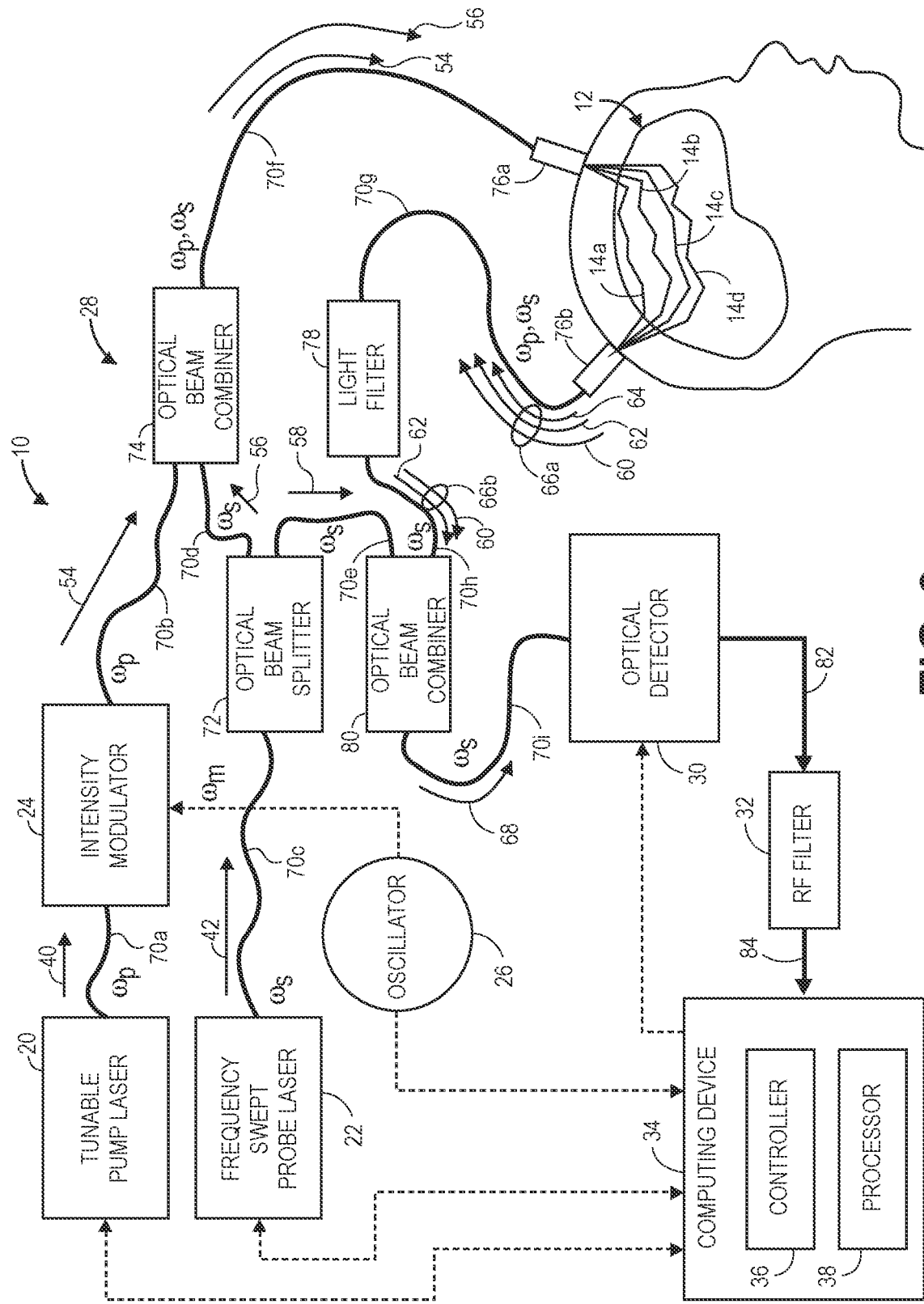
FIG. 3 is a block diagram of an optical measurement system constructed in accordance with one embodiment of the present inventions.

Referring now to FIG. 3, an embodiment of an optical measurement system 10 constructed in accordance with the present inventions will be described. The optical measurement system 10 is designed to non-invasively acquire physiological-encoded signal light (i.e., signal light representative of a physiologically-dependent optical parameter) in an anatomical structure 12, e.g., brain tissue, processing the physiological-encoded signal light, and determining the presence and depth of a physiological event in the anatomical structure 12 based on the processed physiological-encoded signal light. The optical measurement system 10 is a holographic optical system (i.e., a system that mixes detected signal light against reference light in order to increase the signal-to-noise ratio (SNR) of the relevant signal). As such, the optical measurement system 10 focuses on the measurement of multiple-scattered signal light of a depth-correlated optical path length, and is capable of detecting physiological events in tissue at a penetration depth of multiple centimeters, as opposed to ballistic signal light measured by a traditional Optical Coherence Tomography (OCT) system.

In the illustrated embodiment, the anatomical structure 12 is a brain, in which case, the optical measurement system 10 may identify the presence and location of neural activity within the brain 12. Although for exemplary purposes, the optical measurement system 10 is described as acquiring physiological-encoded data from brain tissue, variations of such optical measurement system 10 may be used to acquire physiological-encoded data from other anatomical structures of a human body, animal body, and/or biological tissue.

In the illustrated embodiment, the physiological-encoded data acquired by the optical measurement system 10 is neural-encoded data, and the physiological event is a fast-neural signal (i.e., perturbations in the optical properties of neural tissue caused by mechanisms related to the depolarization of neural tissue, including, but not limited to, cell swelling, cell volume change, changes in membrane potential, changes in membrane geometry, ion redistribution, birefringence changes, etc.), although in alternative embodiments, the physiological event may be a slower hemodynamic change, e.g., Doppler shift due to moving blood flow, changes in blood volume, metabolism variations such a blood oxygen changes. However, as will be described in further detail below, the optical measurement system 10, when properly tuned to a specific type of physiological event, is capable of decoding light propagating through a user's brain to detect any physiological event that causes a change in an optical property of the brain 12.

The neural activity information (or the acquired neural-encoded data from which it is derived) may be transmitted to external programmable devices for use (e.g., computed, processed, stored, etc.) therein, e.g., medical devices, entertainment devices, neuromodulation stimulation devices, lie detection devices, alarm systems, educational games, brain interface devices, etc., and/or may be used internally to adjust the detection parameters of the optical measurement system 10, such as increasing or decreasing the strength of the optical source and/or data compression and/or analysis, such a Fast Fourier Transform (FFT) and/or statistical analysis.

Although the optical measurement system 10, for purposes of brevity, is described herein as acquiring neural-encoded data from the brain 12 by using a single fixed source/detector-array pair arrangement to create one bundle of detected optical paths 14a-14d (generically, 14) through the brain 12 in a single measurement period, in a practical implementation capable of localizing the fast-neural signal in an x-y plane along the surface of the brain, variations of the optical measurement system 10 may utilize more complex source-detector arrangements (e.g., single-source multi-detector, multi-source single-detector, or multi-source multi-detector) to simultaneously create multiple bundles of detected optical paths 14 spatially separated from each other within the brain 12, in a single measurement period, or may utilize a movable source-detector arrangement to sequentially create multiple sample paths over several measurement periods, as described in U.S. patent application Ser. No. 16/379,090, entitled "Non-invasive Frequency Domain Optical Spectroscopy For Neural Decoding," and U.S. patent application Ser. No. 16/392,963, entitled "Interferometric Frequency-Swept Source and Detector in a Photonic Integrated Circuit," which are expressly incorporated herein by reference. Thus, in a practical implementation, the optical detection system 10 may detect and localize physiological events associated with neural activity within the brain, including fast-neural signals, in three-dimensions, with two of the dimensions represented as an x-y plane spanning the surface of the brain 12 encoded within the spatially separated multiple sample paths and the third dimension (z-dimension or depth into the brain 12) being encoded within frequency components of photons propagating along the optical paths 14.

The optical measurement system 10 generally comprises a first optical source 20 (in the form of pump laser), a second optical source 22 (in the form of a probe laser), a modulator 24, an oscillator 26, an interferometer 28, an optical detector 30, a RF filter 32, and a computing device 34, which all operate together to non-invasively detect the presence and depth of a fast-neural signal within the brain 12. In this embodiment, only a single source-detector arrangement is described, although as discussed above, the optical measurement system 10 may employ a variety of source-detector arrangements.

The computing device 34 comprises a controller 36, a processor 38, a memory (not shown), a display (not shown), and an input device (not shown). The computing device 34 can, e.g., be a computer, tablet, mobile device, or any other suitable device for processing the detected neural signal information. The computing device 34 can be local to the user or can include components that are non-local to the user. For example, in at least some embodiments, the user may operate a terminal that is connected to a non-local computing device. In other embodiments, the memory can be non-local to the user. The computing device 34 can utilize any suitable processor 38, including one or more hardware processors that may be local to the user or non-local to the user or other components of the computing device 34. The processor 38 is configured to execute instructions provided to the processor 38, as described below.

Any suitable memory can be used for the computing device 34. The memory can be a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal. The term "modulated data signal" can include a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display can be any suitable display device, such as a monitor, screen, or the like, and can include a printer. In some embodiments, the display is optional. In some embodiments, the display may be integrated into a single unit with the computing device 34, such as a tablet, smart phone, or smart watch. The input device can be, for example, a keyboard, mouse, touch screen, track ball, joystick, voice recognition system, or any combination thereof, or the like.

Although the controller 36 and processor 38 are described herein as being separate components, it should be appreciated that portions or all functionality of the controller 36 and processor 38 may be performed by a single component. Furthermore, although all of the functionality of the controller 36 is described herein as being performed by a single component, and likewise all of the functionality of the processor 38 is described herein as being performed by a single component, such functionality each of the controller 36 and the processor 38 may be distributed amongst several computing devices. Moreover, it should be appreciated that those skilled in the art are familiar with the terms "controller" and "processor," and that they may be implemented in software, firmware, hardware, or any suitable combination thereof.

The pump laser 20, e.g., first optical source, is configured for generating pump source light 40, and the probe laser 22, e.g., second optical source, is configured for generating probe source light 42. Each of the pump laser 20 and probe laser 22 may receive power from a drive circuit (not shown), which may include control inputs for receiving control signals from the controller 36 that cause the respective lasers 20, 22 to emit the pump source light 40 and probe source light 42 at a selected time, duration, intensity, or coherence length. In one embodiment, each of the lasers 20, 22 is a continuous wave (CW) laser source, although in alternative embodiments, either of the lasers 20, 22 may be a pulsed wave (PW) laser, in which case, the pulse width of the respective pump source light 40 or probe source light 42 can be at least as long as the measurement period. Preferably, if a PW laser is used, the width of the pulse is greater than 100 ps, such that resulting frequency spectrum of the signal to be detected is not blurred due to dispersion of the pulse through the tissue. However, CW laser sources are generally less than expensive than PW laser sources, and thus, CW laser sources are preferred.

Each of the lasers 20, 22 may take the form of, e.g., a distributed feedback (DFB) laser, although other lasers, e.g., a diode-pumped solid-state (DPSS) laser, a laser diode (LD), a titanium sapphire laser, and/or similar laser to achieve very narrow spectral linewidths and extremely high amplitude stability, among other optical sources, such as a light emitting diode (LED), a super luminescent light emitting diode (sLED), a micro light emitting diode (mLED), etc., may be used.

Each of the lasers 20, 22 may have either a predefined coherence length or a variable coherence length. Since the goal of the optical measurement system 10 is to measure optical and dynamic properties deep within the brain tissue, as opposed to acquiring images of the brain tissue at a shallow depth as obtained by typical OCT systems, each of the lasers 20, 22 preferably has an instantaneous spectral linewidth and tuning range narrower by several orders of magnitude than in typical OCT systems, enabling the measurement of distinctly longer optical path lengths (of up to tens of centimeters) at the cost of reduced resolution (of the order of millimeters). Preferably, each of the lasers 20, 22 has a coherence length of at last 30 cm, an instantaneous spectral linewidth of less than 2 nm, and preferably less than 0.5 nm, and an optical wavelength bandwidth greater than 3 μm, and preferably greater than 30 μm.

Each of the pump source light 40 and probe source light 42 may be ultraviolet (UV) light, visible light, and/or near-infrared and infrared light, and may have any suitable wavelength, e.g., in the range of 350 nm-1800 nm. Each of the pump source light 40 and probe source light 42 has a narrow optical spectrum, preferably close to monochromatic in nature. Notwithstanding the foregoing, it is preferred to select the difference between the respective optical frequencies $\omega_p$, $\omega_s$ of the pump source light 40 and probe source light 42 to be equal to the vibrational frequency mode $\Omega$ of the molecules in the anatomical structure, e.g., user's brain, to be detected, and in this case, the proteins in the neuronal membrane. As discussed above, such selection of optical frequencies for the pump source light 40 and probe source light 42 will amplify the inelastic scattering of the probe source light 42 by the neuronal membranes with which both the pump source light 40 and probe source light 42 coincide, in effect, amplifying the Raman signal. Thus, the respective optical frequencies $\omega_p$, $\omega_s$ of the pump source light 40 and probe source light 42 can be selected to maximize sensitivity to the specific physiological event of interest, and in this case, a fast-neural signal.

Notably, because it is ultimately the difference between the respective optical frequencies $\omega_p$, $\omega_s$ of the pump source light 40 and probe source light 42 that is selected to maximize the sensitivity to the fast-neural signal to be detected, the optical frequencies $\omega_p$, $\omega_s$, themselves, may be selected to maximize propagation of both the pump source light 40 and probe source light 42 within the brain 12. That is, the optical frequencies $\omega_p$, $\omega_s$ can be selected to fall within the optical transparency window of brain tissue. The optical transparency of living tissue is known to be in the range of 650 nm-1200 nm, since at shorter optical wavelengths, light is strongly absorbed by hemoglobin in blood, while at longer wavelengths, light is strongly absorbed by water. In the case where maximum sensitivity to a physiological event, e.g., a fast-neural signal, falls outside of this optical transparency window, the optical frequencies $\omega_p$, $\omega_s$ of the pump source light 40 and probe source light 42 can be selected to fall within this optical transparency window, yet still provide maximum sensitivity to the physiological event.

In one embodiment, the pump laser 20 is tunable, and thus has a tuning range to ensure that difference between the optical frequencies $\omega_p$, $\omega_s$ of the pump source light 40 and probe source light 42 is equal to the molecular vibration frequency of interest $\Omega$, and in this case, approximately 88 THz to maximize sensitivity of the optical measurement system 10 to the fast-neural signal. Furthermore, by making the pump laser 20 tunable, the optical measurement system 10 is made more versatile; that is, the pump laser 20 can be tuned to identify other molecular fingerprints for better detection probability.

The intensity modulator 24 is configured for intensity modulating the pump source light 40 output by the pump laser 20 at a modulation frequency $\omega_m$ in accordance with the oscillator 26, and outputting intensity modulated pump sample light 54. The intensity modulator 24 may be optically coupled to the pump source light 40 via an optical fiber 70a. The oscillator 26 outputs a signal having a fixed or variable frequency. The oscillator 26 may be variable, in which case, it may have a control input for receiving control signals from the controller 36 that cause the oscillator 26 to output a signal at a defined frequency. Alternatively, the oscillator 26 may be fixed, in which case, it will output a signal having a fixed frequency. The pump sample light 54 will have a time-varying intensity in accordance with the equation:

$$I_p(t) = I_{p0}\left[\frac{1}{2} - \frac{M}{2}\cos(\omega_m t)\right]e^{-i\omega_p t}, \qquad [4]$$

where $I_{p0}$ is the DC intensity of the pump sample light 54, M is the intensity modulation amplitude in accordance with the limit (0<M<1), $\omega_m$ is the intensity modulation frequency, and $\omega_p$ is the optical frequency of the pump sample light 54, with $\omega_m \ll \omega_p$.

The controller 36 instructs the probe laser 22 to sequentially generate probe source light 42 over a range of optical frequencies, and in this embodiment, sweep the probe source light 42 over a range of optical path lengths, i.e., over a range of optical frequencies, with the center optical frequency being selected to generate the Raman signal as discussed above with respect to FIG. 2. The probe laser 22 may receive input current from a drive circuit (not shown), e.g., a laser diode current driver. The controller 36 may modulate such input current using a sinusoidal waveform having a suitable frequency, e.g., 50 KHz. The sweep rate of the probe laser 22 defines a measurement period of the optical measurement system 10 in accordance with the equation:

$$\tau = 1/R, \qquad [5]$$

where z is the measurement period, and R is the unidirectional rate (forward sweep or reverse sweep).

The probe sample light 56 will have a time-varying intensity in accordance with the equation:

$$I_s = I_{s0} e^{-i[\omega_s + R]t}, \qquad [6]$$

where $I_{s0}$ is the DC intensity of the probe sample light 56, R is the optical frequency sweep rate, and $\omega_s$ is the optical frequency of the probe sample light 56.

Figure 4:
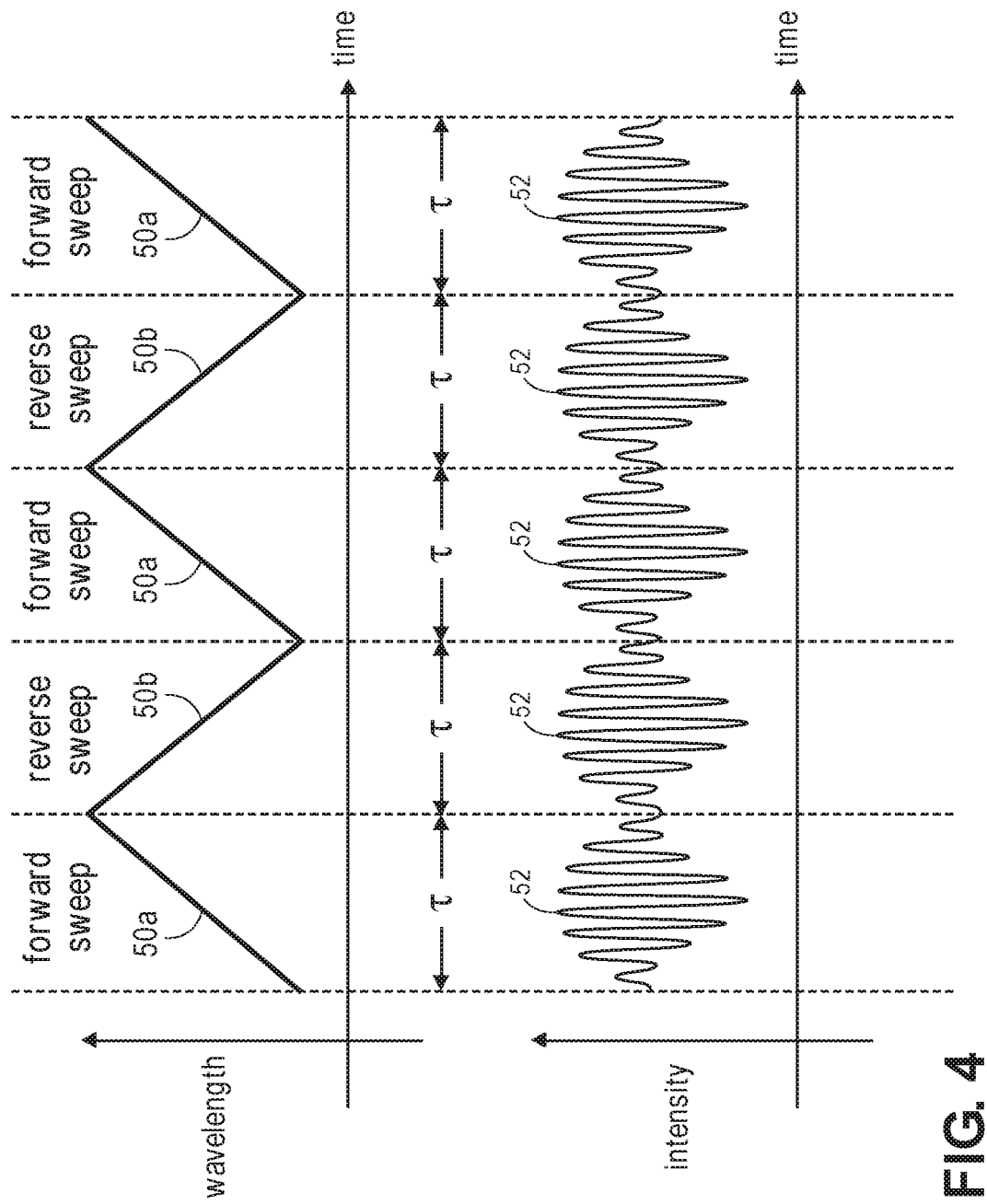
FIG. 4 is a timing diagram illustrating the optical sweeps performed by the optical measurement system of FIG. 3, and fringe patterns in interference light patterns resulting from the optical sweeps.

As illustrated in FIG. 4, the probe laser 22 sweeps across a range of optical frequencies during the measurement period z to achieve interferograms to be used for time-of-flight (TOF) detection, as will be described in further detail below. In the illustrated embodiment, the measurement periods z are respectively defined by both forward sweep 50a (low to high wavenumbers) and rearward sweeps 50b (high to low wave numbers) of the probe laser 22, thereby maximizing the usage of the full sweep range of the probe laser 22. However, in alternative embodiments, all of the measurement periods $\tau$ are defined by either forward sweeps 50a or reverse sweeps 50b (but not both), such that there are idle time intervals between sequential measurement periods $\tau$ equal to the time period of a unilateral sweep R. However, because the data throughput is generally limited by the detection and processing scheme, the existence of the idle time intervals between the measurement periods z will generally not limit the data throughput of the optical measurement system 10. As will be described in further detail below, interference light created by the dynamic interference between the swept probe source light 42 and reference light results in a dynamic fringe pattern 52 (i.e., a fringe pattern 52 having a frequency component that varies over time) for each optical wavelength sweep 50.

It should be noted that range of optical frequencies over which the probe source light 42 is swept should be sufficient to provide a given time-of-flight (TOF) resolution, typically in the hundreds of GHz (e.g., 100 GHz) around the central optical frequency $\omega_s$. The range of optical frequencies over which the probe source light 42 is swept is narrow enough, such that entire range falls within the Raman band of the molecules of interest as to not interfere with the molecular spectroscopy. In the case where the molecules of interest are the proteins in the neural membrane, the central optical frequency $\omega_s$ of the probe source light 42 should be selected, such that the difference between the optical frequency $\omega_p$ of the pump source light 40 and the central optical frequency $\omega_s$ of the probe source light 42 coincides with the center of the Raman band of the neurons (in this case, at approximately 88 THz) to not only maximize sensitivity of the optical measurement system 10 to a fast-neural signal, but also to maximize the tolerance of the range over which the optical frequencies of the probe source light 42 are swept, and the optical frequency range of the probe source light 42 has a width less than the bandwidth of the Raman band centered about 88 THz (approximately 1.5 THz). If the optical frequency range of the probe source light 42 is 100 GHz, which is sufficient to provide the necessary TOF (depth) resolution, the Raman band of the neural membrane will be fifteen times wider than width of the optical frequency range. As such, the molecular signature will typically be much wider than the optical frequency range of the probe source light 42.

Referring back to FIG. 3, the interferometer 28 is configured for path-length selecting (depth resolution) the Raman signal emitted by the brain 12. To the end, the interferometer 28 is configured for splitting the frequency swept probe source light 42 into frequency swept probe sample light 56, which propagates along a sample arm of the interferometer 28, and frequency swept probe reference light 58, which propagates along a reference arm of the interferometer 28. The interferometer 28 is further configured for combining intensity modulated pump sample light 54 and the frequency swept probe sample light 56, and delivering the combined pump sample light 54 and probe sample light 56 into the brain 12 (preferably through the scalp and skull), such that a portion of the probe sample light 56 is inelastically scattered by the brain 12 as physiological-encoded (in this case, neural-encoded) signal light 60 (i.e., the Raman signal) at the optical frequency $\omega_s$ and intensity modulated at the modulation frequency $\omega_m$ of the intensity modulated pump sample light 54, a portion of the probe sample light 56 is elastically scattered by the brain 12 as non-modulated background light 62 at the optical frequency $\omega_s$, and a portion of the pump sample light 54 is scattered (elastically and inelastically) by the brain 12 as background light 64 intensity modulated at the modulation frequency $\omega_m$ of the intensity modulated pump sample light 54. The neural-encoded signal light 60, non-modulated background light 62, and modulated background light 64 combine and exit the brain 12 as combined sample light 66a. The interferometer 28 is further configured for filtering out the intensity modulated background light 64 from the combined sample light 66a exiting the brain 12, resulting in filtered sample light 66b, and combining the filtered sample light 66b and the probe reference light 58 into interference light 68 having a plurality of frequency components encoded with a plurality of different depths of the brain 12.

As will be described in further detail below, a band of these frequency components are associated with the contribution of the neural-encoded signal light 60 (i.e., the inelastic scattering of the probe sample light 56 that creates the Raman signal) to the interference light 68, and will thus, be used to determine the presence and depth of a fast-neural signal within the brain 12, and another band of these frequency components are associated with the contribution of the non-modulated background light 62 (i.e., the elastic Rayleigh scattering of the probe sample light 56) to the interference light 68 that is typically measured in conventional iNIRS systems to determine the presence and depth of other types of slower physiological events (e.g., hemodynamic events) within the brain 12, but only serve as undesirable background noise in the optical measurement system 10 described herein.

In this implementation, the interferometer 28 is optical fiber-based (i.e., uses optical fibers to direct light between the components), although in alternative embodiments, the interferometer 28 may direct light via free-space propagation between the components using optics, such as mirrors, as further illustrated in U.S. patent application Ser. No. 16/266,818, entitled "Ultrasound Modulating Optical Tomography Using Reduced Laser Pulsed Duration," U.S. patent application Ser. No. 16/299,067, entitled "Non-Invasive Optical Detection Systems and Methods in Highly Scattering Medium," and U.S. patent application Ser. No. 16/382,461, entitled "Non-Invasive Optical Detection system and Method," which are expressly incorporated herein by reference.

The interferometer 28 comprises a first input optical fiber 70b that optically couples the interferometer 28 to the pump laser 20 for receiving the intensity modulated pump source light 40 from the pump laser 20; a second input optical fiber 70c that optically couples the interferometer 28 to the probe laser 22 for receiving the frequency swept probe source light 42 from the probe laser 22; an optical fiber-based optical beam splitter 72 for splitting the probe source light 42 into the probe sample light 56 and the probe reference light 58; and a sample arm optical fiber 70d and a reference arm optical fiber 70e for respectively propagating the probe sample light 56 and probe reference light 58 along the sample arm and reference arm of the interferometer 28.

The optical beam splitter 72 may not necessarily split the source light 42 equally into the probe sample light 56 and probe reference light 58, and it may actually be more beneficial for the optical beam splitter 72 to split the probe source light 42 unevenly, such that the intensity of the probe sample light 56 is less than the intensity of the probe reference light 58 (e.g., 99/1 power ratio), since much of the probe sample light 56 will be lost after passing through the user's head. That is, the intensity of the probe sample light 56 should be boosted relative to the probe reference light 58 to compensate for the losses incurred by the probe sample light 56 as it passes through the user's head and the fact that only a small portion of signal light (described below) exiting the user's head will be detected.

The interferometer 28 further comprises an optical beam combiner 74 configured for combining the pump sample light 54 and probe sample light 56 and which can be represented as follows: [7] $A*I_p(t)+B*I_s(t)$, where A and B are constants, $I_p(t)$ is the time-varying intensity of the pump sample light 54 in accordance with equation [4], and $I_s(t)$ is the time-varying intensity of the probe sample light 56 in accordance with equation [6].

The interferometer 28 further comprises another sample arm optical fiber 70f for propagating the combined pump sample light 54 and probe sample light 56 further along the sample arm of the interferometer 28; and a single output port 76a configured for delivering the combined probe sample light 56 and pump sample light 54 into the brain 12, such that the combined probe sample light 56 and pump sample light 54 scatter diffusively through the brain 12, and back out again, exiting as the combined sample light 66a, which comprises the neural-encoded signal light 60, non-modulated background light 62, and modulated background light 64; and a single input port 76b configured for receiving the combined sample light 66a from the brain 12.

Significantly, as it scatters diffusively through the brain 12, various portions of the probe sample light 56 will take different optical paths 14a-14d through the brain 12. For purposes of brevity, only four sample light portions are illustrated as traveling along optical paths 14a-14d of different lengths (from shallow to deep), which combines into the exiting neural-encoded signal light 60, although it should be appreciated that the diffused pump sample light 54 will travel along many more optical paths through the brain 12, thereby encoding the intensity-modulated signal light 60 with depth information, along with the neural activity, as will be described in further detail below. Although the modulated background light 64 will likewise scatter diffusively along various different paths through the brain 12, the modulated background light 64 resulting from the pump sample light 54 does not contain any information that is used by the optical measurement system 10, and thus, such paths are irrelevant and not shown. Rather, it is only relevant that the pump sample light 54 is incident with the probe sample light 56 on relevant tissue in the brain 12 to cause inelastic scattering of, and thus neural encode, the probe sample light 56 as the intensity-modulated signal light 60.

The interferometer 28 further comprises additional sample arm optical fibers 70g, further along the sample arm of the interferometer 28; a light filter 78 70h for propagating the combined sample light 66a from the single input port 76b further along the sample arm of the interferometer 28; a light filter 78 configured for filtering out the modulated background light 64 from the combined sample light 66a and outputting filtered sample light 66b; an optical beam combiner 80 configured for combining the filtered sample light 66b and probe reference light 58 via superposition to generate the interference light 68, which as will be described in further detail below, has frequency components encoded with different depths of the brain 12; and an output optical fiber 70i for outputting the interference light 68 from the interferometer 28.

The optical detector 30 is configured for detecting the interference light 68 and outputting an electrical signal 82 containing the frequency components of the interference light 68. In the illustrated embodiment, the optical detector 30 takes the form of a balanced optical detector that removes the DC component from the interference light 68, essentially extracting the signal-carrying oscillation frequency (i.e., AC) components from the interference light 68. In one embodiment, the balanced detector 30 splits interference light 68 into first and second phase-modulated interference light that are out of optical phase by 180 degrees, detects the first and second phase-modulated interference light on two different detectors, subtracts the resulting first and second phase-modulated electrical signals via an arithmetic unit (e.g., a subtractor) to remove the DC component and obtain the AC component of the electrical signal, and outputs the electrical signal 82.

The balanced detector 30 includes control inputs (not shown) for receiving control signals from the controller 36, such that detection of the spatial components of the interference light 68 can be coordinated with the delivery of the pump sample light 54 and probe sample light 56 into the brain 12, and further can be operated to sample the interference light 68 at various times throughout each optical wavelength sweep of the probe sample light 56. For example, if the sampling rate of the balanced detector 30 is 100 MHz, and the sweep repetition rate of the probe laser 22 is 1 MHz, then the balanced detector 30 will obtain one hundred values for the neural-encoded electrical signal 82.

Figure 5B:
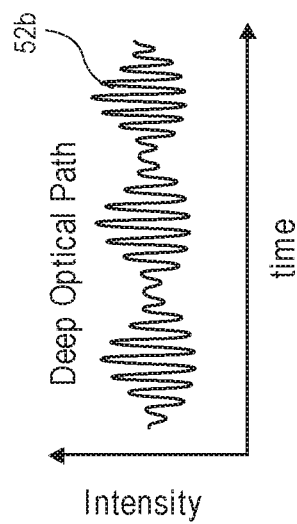
FIG. 5B is a timing diagram illustrating a series of fringe patterns of an interference light pattern corresponding to a deep optical path.
Figure 5A:
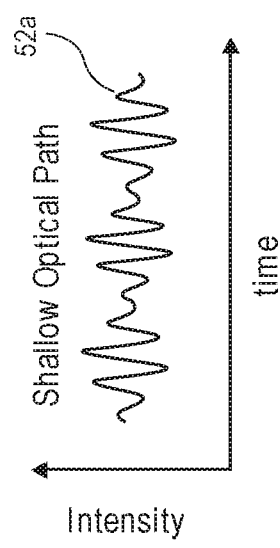
FIG. 5A is a timing diagram illustrating a series of fringe patterns of an interference light pattern corresponding to a shallow optical path.

As discussed above with respect to FIG. 4, the interference light 68, which is created by the dynamic interference between the swept probe sample light 56 and probe reference light 58 results in a dynamic fringe pattern 52 for each optical wavelength sweep 50. The frequency at which the fringe pattern 52 oscillates for any given optical pathlength difference $\Delta L$ between the sample arm and the reference arm (i.e., TOFs) corresponds to the frequency component in the interference light 68 correlated to that optical pathlength difference $\Delta L$. The frequency of the fringe pattern 52 increases with the optical pathlength difference $\Delta L$, and thus the depth of the optical path 14. Thus, a relatively shallow optical path (e.g., the optical path 14a in FIG. 3) will yield, over a series of sweeps, a series of fringe patterns 52a with a relatively slow oscillation frequency (see FIG. 5A), whereas a relatively deep optical path (e.g., the optical path 14d in FIG. 3) will yield, over a series of sweeps, a series of fringe patterns 52b with a relatively fast oscillation frequency (see FIG. 5B).

Figure 6A:
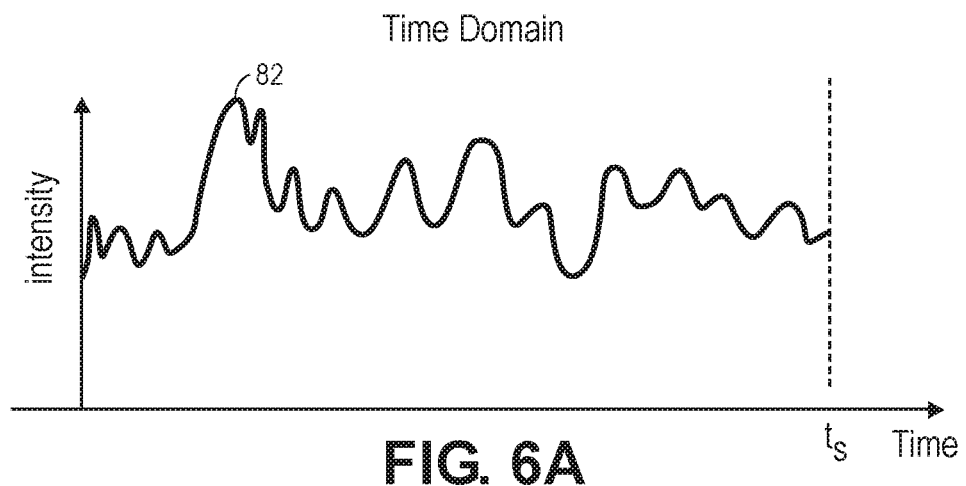
FIG. 6A is a timing diagram illustrating interference light generated by the optical measurement system of FIG. 3 in the time domain.

As briefly discussed above, the interference light 68, and thus the electrical signal 82 output by the balanced detector 30, contains a band of frequency components that are associated with the contribution of the desirable neural-encoded signal light 60 to the interference light 68, and another band of these frequency components are associated with the contribution of the undesirable non-modulated background light 62 to the interference light 68. For example, the electrical signal 82 output by the balanced detector 30 across one frequency sweep of the probe source light 42 (from t=0 to t=$t_s$) is illustrated in the time domain in FIG. 6A. The electrical signal 82 is highly variable from t=0 to t=$t_s$, and can be characterized as a composite of all of the fringe patterns 52 across the frequency sweep. As demonstrated in the frequency domain in FIG. 6B, the electrical signal 82 contains both a band of frequency components 86a associated with the neural-encoded signal light 60 (i.e., the Raman signal), and a band of frequency components 86b associated with the non-modulated background light 62. It is preferred that the frequency bands 86a, 86b not overlap each other, such that the desirable frequency band 86a can be cleanly extracted from the interference light 68, i.e., from the electrical signal 82.

Figure 6B:
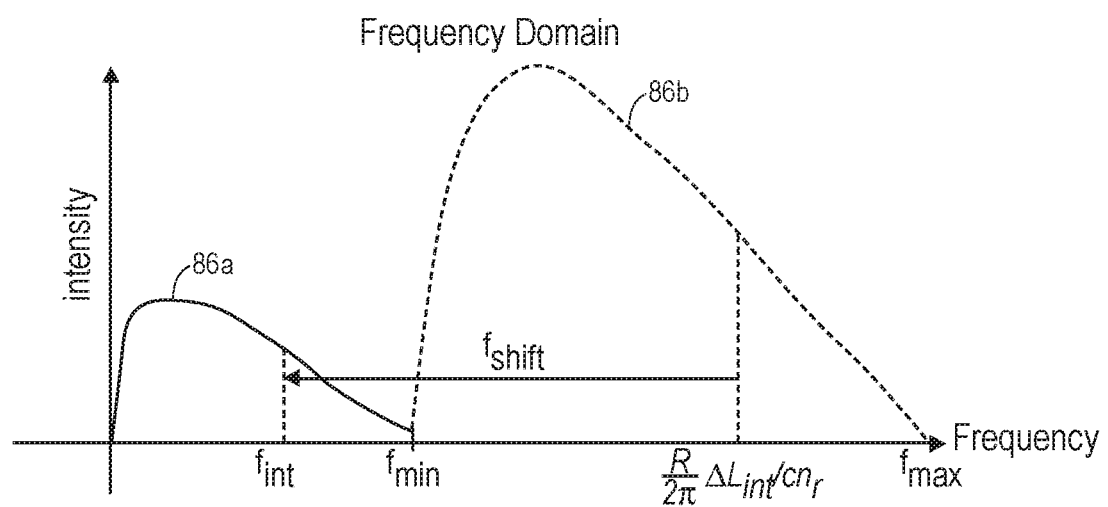
FIG. 6B is a timing diagram illustrating the interference light of FIG. 6A in the frequency domain.

Notably, the intensity modulation of the pump sample light 54 advantageously up frequency shifts and down frequency shifts the desirable frequency band 86a of the interference light 68 away from the undesirable frequency band 86b of the interference light 68 (only the down frequency shift $f_{shift}$ of the frequency band 86a shown in FIG. 6B) by the modulation frequency $\omega_m$ ($f_{shift}=\omega_m/2\pi$). Thus, the modulation frequency $\omega_m$ of the pump source light 40 should be judicially selected, such that the frequency bands 86a, 86b do not overlap in accordance with the equation:

$$\omega_m \geq 2\pi(f_{max}-f_{min}), \quad [8]$$

where $$f_{max} = \frac{R}{2\pi}\Delta L_{max}/cn_r, \text{ and} \quad [9]$$

$$f_{min} = \frac{R}{2\pi}\Delta L_{min}/cn_r, \quad [10]$$

and where R is the optical frequency sweep rate of the probe source light 42, $\Delta L_{max}$ is the maximum path length difference between the sample arm and reference arm of the interferometer 28, and $\Delta L_{min}$ is the minimum path length difference between the sample arm and reference arm of the interferometer 28. The maximum and minimum path length differences $\Delta L_{max}$ and $\Delta L_{min}$ can be set by selecting the lengths of the optical fibers 68.

To prevent aliasing, which would otherwise occur if the frequency band 86a is shifted into the negative frequency region, the minimum frequency $f_{min}$ of the undesirable frequency band 86b should be greater than one-half the maximum frequency $f_{max}$ of the desirable frequency band 86a.

Notably, as will be described in further detail below, the depth in the brain 12 at which the fast-neural signal is to be determined can be selected by analyzing the desirable frequency component 86a at the frequency of interest $f_{int}$ in accordance with the equation:

$$f_{int} = \frac{\frac{R}{2\pi}\Delta L_{int}}{cn_r} - f_{shift},$$ [11]

where $\Delta L_{int}$ is the path length difference of interest (correlated to the depth in the brain 12) between the sample arm and reference arm of the interferometer 28.

The RF filter 32 is configured for extracting the desirable frequency band 86a from the electrical signal 82, and thus, the detected interference light 68, by filtering out the undesirable frequency band 86b, and outputting an electrical signal 84 containing only the desirable frequency band 86a, i.e., the first frequency components associated with the contribution of the neural-encoded signal light 60 (i.e., the inelastic scattering of the probe sample light 56 that creates the Raman signal) to the interference light 68. In the illustrated embodiment, the RF filter 32 is a low-pass filter having a cutoff frequency equal to or less than the minimum frequency $f_{min}$ of the undesirable frequency band 86b.

The processor 38 is configured for digitizing the electrical signal 84 to create data values respectively comprising the first frequency components (i.e., different frequencies of interest $f_{int}$), analyzing the detected interference light 68, and in particular, the desirable frequency band 86a contained in the electrical signal 84 output by the RF filter 32 (i.e., the data values), and based on this analysis, determining a presence and depth of a fast-neural signal within the brain 12. In one embodiment, the processor 38 is configured for deriving the oscillation frequency component intensity values by computing a Fourier transform of the electrical signal 84 output by the filter 32.

Figure 7B:
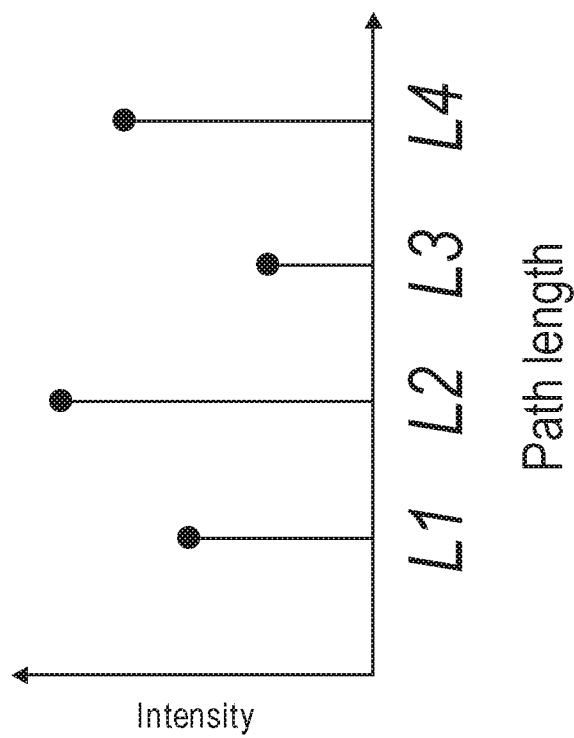
FIG. 7B is a diagram illustrating exemplary optical path length intensities corresponding to the exemplary frequency components of FIG. 7A.
Figure 7A:
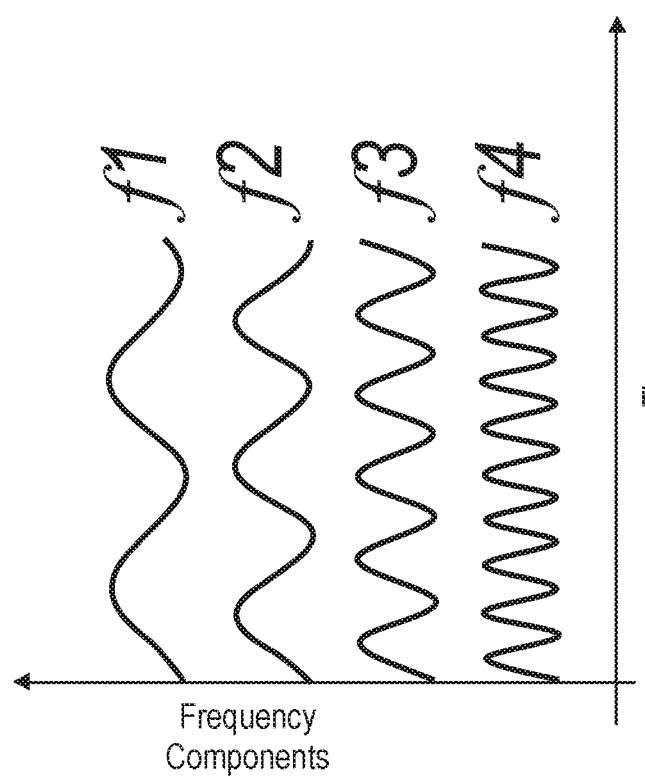
FIG. 7A is a diagram illustrating exemplary frequency components of an interference light pattern generated by the optical measurement system of FIG. 3.

Significantly, the frequency band 86a of the interference light 68 is respectively encoded with different depths of the brain 12. For example, four exemplary frequency components f1-f4 (FIG. 7A) respectively correspond to four exemplary intensities of the light at four different optical path lengths L1-L4 (FIG. 7B) (which directly correlate to depths of the fast-neural signal within the brain 12). The processor 38 is configured for deriving the intensity value of each of the frequency components f1-f4 in the frequency band 86a of the interference light 68, and determining a depth of the fast-neural signal within the brain 12 (correlated to the optical path lengths L1-L4 (i.e. TOFs), at least partially, based on these frequency component intensities.

In one embodiment, the processor 38 determines depth of the fast-neural signal (and alternatively hemodynamic changes), and thus the neural activity, within the brain 12, e.g., by comparing the current signal intensity-frequency profile (in this case, the computed means of the derived oscillation frequency component intensity value arrays of the currently detected interference light 68) with a user-specific baseline signal intensity-frequency profile (e.g., a previously acquired signal intensity-frequency profile) (in this case, corresponding reference frequency component intensity value arrays of a previously detected interference light 68).

Figure 8A:
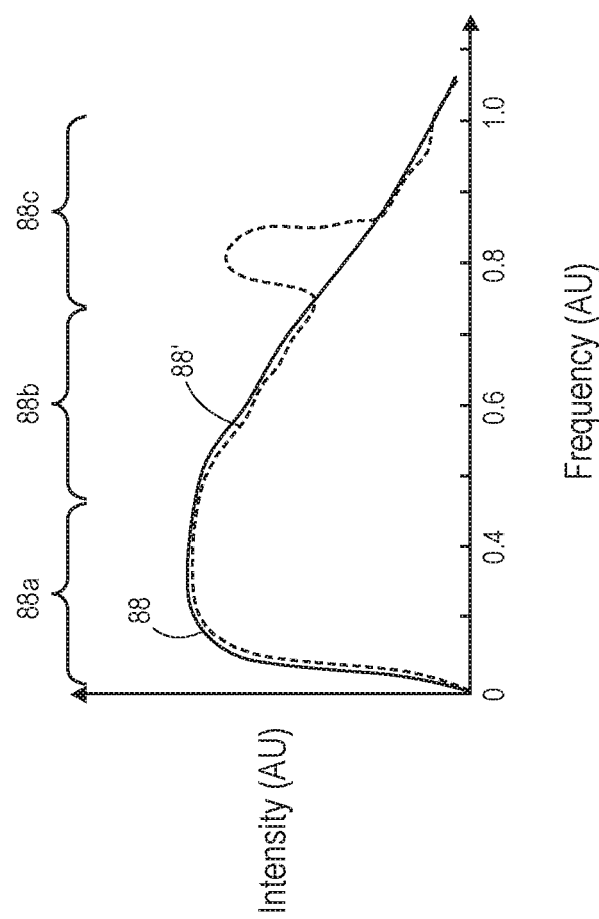
FIG. 8A is a timing diagram illustrating an exemplary signal intensity-frequency profile generated by the optical measurement system of FIG. 3.
Figure 8B:
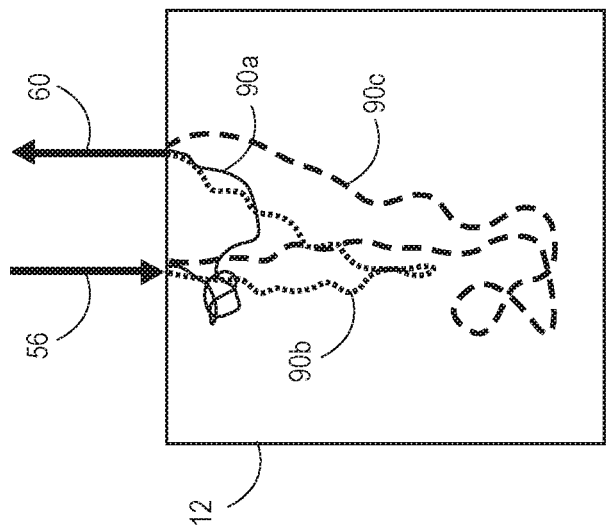
FIG. 8B is a plan view illustrating exemplary path lengths of photons corresponding to different frequency bands of the exemplary signal intensity-frequency profile of FIG. 8A.

For example, referring to FIGS. 8A and 8B, it can be seen that there is a strong correlation between the depth of penetration of photons of the probe sample light 56 within the brain 12 and the shape of a signal intensity-frequency profile 88 corresponding to the desirable frequency band 86a. That is, the signal intensity-frequency profile 88 can be correlated to spatial depth information (i.e., the tail end of the signal intensity-frequency profile 88 contains relatively deep information, whereas the front end of the signal intensity-frequency profile 88 contains relatively shallow information), and thus, the spatial depth of the fast-neural signal along the different optical paths of the probe sample light 56 may be determined. That is, it is known that the occurrence of the fast-neural signal along one of the optical paths of the probe sample light 56 will perturb the photons of the probe sample light 56 at the depth of the fast-neural signal along that optical path, thereby changing the intensity of the photons of the probe sample light 56 having an optical path length corresponding to that depth.

For example, a relatively early frequency band 88a of the signal intensity-frequency profile 88 is weighted for photons that travel a relatively short distance through the brain 12; that is, photons 90a that penetrate superficially into the brain 12; a relatively medial frequency band 88b of the signal intensity-frequency profile 88 is weighted for photons that travel a relatively medial distance through the brain 12; that is, photons 90b that penetrate further into the brain 12; and a relatively high frequency band 88c of the of the signal intensity-frequency profile 88 is weighted for photons that travel a maximum distance through the brain 12; that is, photons 90c that penetrate even further into the brain 12.

Thus, it can be appreciated that the signal intensity-frequency profile 88 contains intensity-optical path length information in which the spatial depth of a fast-neural signal is encoded, and thus, a fast-neural signal that occurs at a certain depth in the brain 12 will cause a corresponding perturbation in the signal intensity-frequency profile 88. For example, as shown in FIG. 8A, there exists a perturbation between the baseline signal intensity-frequency profile 88 in the absence of a fast-neural signal, and a signal intensity-frequency profile 88' in the presence of a fast-neural signal. The fast-neural signal causes a measurable perturbation in the signal intensity-frequency profile 88 in the frequency band 88c, indicating a change in the Raman signal at maximum depth, and thus, a fast-neural signal at this depth, in the brain 12. Thus, in effect, the processor 38 may determine the presence and depth of the fast-neural signal within the brain 12 by comparing the difference between the currently detected interference light 68 and reference (or baseline) interference light (in the absence of the fast-neural signal).

Figure 9:
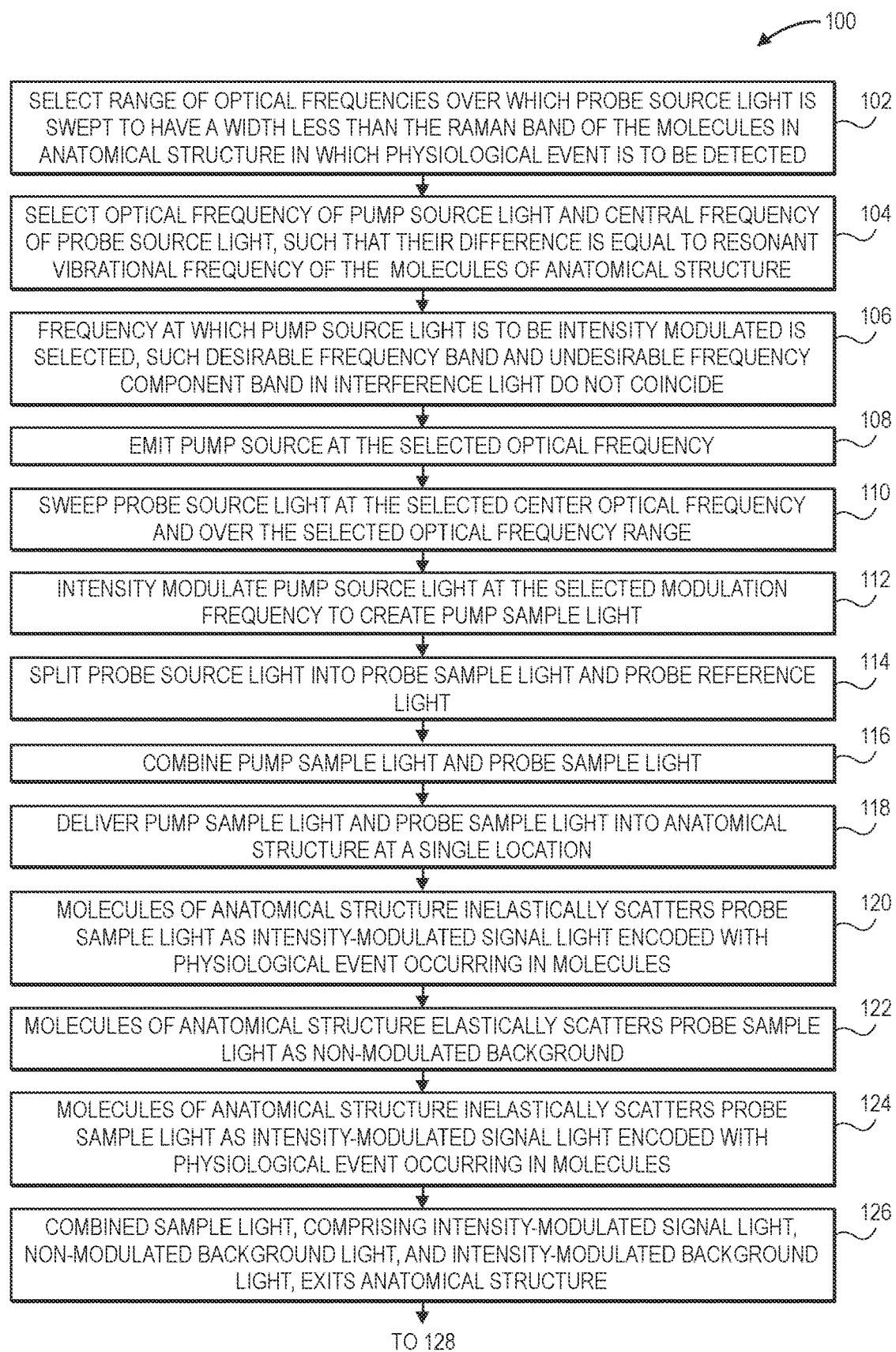
FIG. 9 is a flow diagram illustrating one method used by the optical measurement system of FIG. 3 to non-invasively detect one or more physiological events within an anatomical structure.
Figure 9:
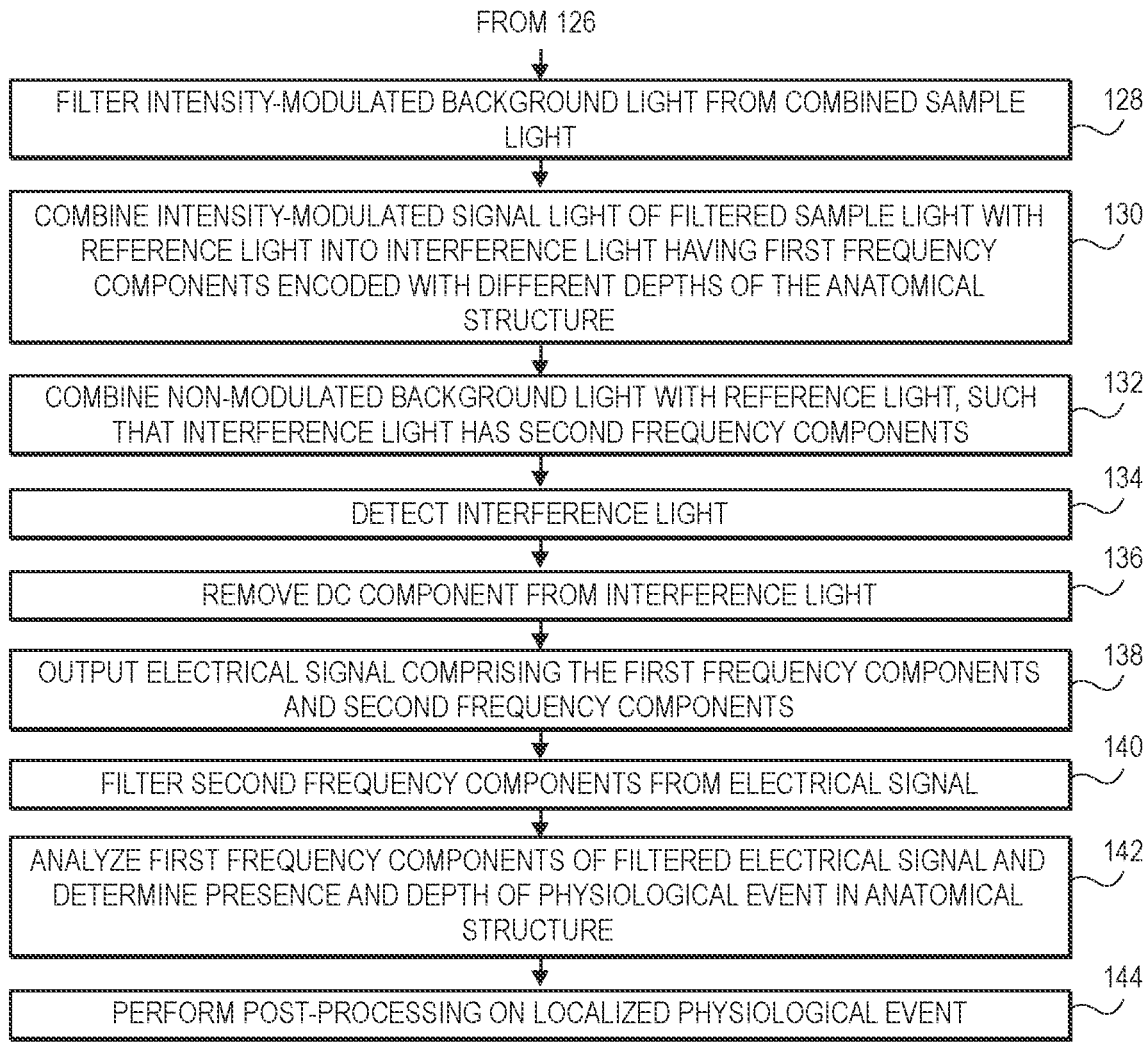

Referring to FIG. 9, having described the structure and function of the optical measurement system 10, one particular method 100 performed by the optical measurement system 10 to non-invasively determine the depth of a physiological event (in this case, a fast-neural signal) in the anatomical structure 12 (in this case, the brain) will now be described.

The range of the optical frequencies over which the probe source light 42 is to be swept is selected to have a width less than the Raman band of the molecules in the brain 12 in which the physiological event is to be detected (step 102). In this case, the physiological event is a fast-neural signal, and thus, range of the optical frequencies over which the probe source light 42 is swept is selected to have a width less than the Raman band of neural membrane proteins (e.g., less than 1.5 THz).

The optical frequency of the pump source light 40 and one of the optical frequencies (e.g., the central optical frequency) of the probe source light 42 are also selected (e.g., by tuning the pump source light 40), such that their difference is equal to the resonant vibrational frequency (e.g., at the center of the Raman band) of the molecules of the brain 12 in which the physiological event is to be detected (step 104). In this case, the physiological event is a fast-neural signal, and thus, the optical frequency of the pump source light 40 and central optical frequency are preferably selected, such the difference between the optical frequency of the pump source light 40 and the central optical frequency of the probe source light 42 is equal to the peak resonant vibrational frequency of the neural membrane proteins (e.g., 88 THz).

The frequency at which the pump source light 40 is to be intensity modulated is selected, such that the band of frequency components of the interference light 68 to which the intensity-modulated signal light 60 contributes (the desirable frequency band) is down frequency shifted away from the band of frequency components of the interference light 68 to which the non-modulated background light 62 contributes (the undesirable frequency band), such that these frequency bands do not coincide with each other (step 106).

Next, the controller 36 sends a control signal to the drive circuit of the pump laser 20 to emit the pump source light 40 at the selected wavelength (optical frequency) and amplitude (step 108), and a control signal to the drive circuit of the probe laser 22 to repeatedly sweep the probe source light 42 at the selected center optical frequency and over the selected optical frequency range during several measurement periods, with each measurement period corresponding to a single optical wavelength range sweep 50 (step 110). The controller 36 also sends a control signal to the oscillator 26 to output a frequency at the selected modulation frequency, such that the intensity modulator 24 intensity modulates the pump source light 40 at the selected modulation frequency to create the pump sample light 54 (step 112).

The interferometer 28 splits the probe source light 42 into probe sample light 56 and probe reference light 58 (e.g., via the optical beam splitter 72) (step 114), combines the pump sample light 54 and probe sample light 56 (e.g., via the optical beam combiner 74) (step 116), and delivers the combined pump sample light 54 and probe sample light 56 into the brain 12 at a single location along a single bundle of optical paths 14 (step 118).

As a result, the molecules of the brain 12 inelastically scatter a portion of the probe sample light 54 as signal light 60 that is intensity modulated at the modulation frequency, such that the intensity-modulated signal light 60 is encoded with a physiological event occurring in the molecules (in this case, a fast-neural signal occurring in the neural membranes) (step 120); molecules of the brain 12 elastically scatter a portion of the probe sample light 56 as non-modulated background light 62 (step 122); and the brain 12 scatters a portion of the pump sample light 56 as intensity-modulated background light 64 at the modulation frequency (step 124). Combined sample light 66*a*, comprising the intensity-modulated signal light 60, the non-modulated background light 62, and the intensity-modulated background light 64, exits the brain 12 (step 126). The light filter 78 then filters the intensity-modulated background light 64 from the combined sample light 66*a* and outputs filtered sample light 66*b* (step 128).

The interferometer 28 combines, during each of the measurement periods (i.e., each optical wavelength sweep 50), the intensity-modulated signal light 60 of the filtered sample light 66*b* and the reference light 58 into interference light 68 having a first plurality of frequency components encoded with a plurality of different depths of the brain 12 (step 130), and the non-modulated background light 62 and the reference light 58, such that the interference light 68 has second plurality of frequency components (step 132).

The balanced detector 30 then detects the interference light 68 (step 134), removes the DC component from the interference light 68 (step 136), and outputs the electrical signal 82 comprising the first plurality of frequency components and second plurality of frequency component (step 138). The RF filter 32 filters the second frequency components from the electrical signal 82 output by the balanced detector 30 and outputs the electrical signal 84 (step 140).

The processor 38 then analyzes the first frequency components of the electrical signal 84 (i.e., the frequencies of interest $f_{int}$) output by the RF filter 32, and based on this analysis, determines the presence and the depth of the fast-neural signal within the brain 12 (step 142). For example, the processor 38 may transform the electrical signal 84 from the time domain into the frequency domain (by computing a Fourier transform of the electrical signal 84 to acquire the frequency components), and analyze the electrical signal 84 in the frequency domain at one or more of the first frequency components. The processor 38 may determine the presence and depth of the fast-neural signal within the brain 12 by comparing the first frequency components to reference frequency components. In the case where multiple detected optical path bundles 14 through the brain 12 are created using complex source-detector arrangements (e.g., single-source multi-detector, multi-source single-detector, or multi-source multi-detector) to simultaneously create multiple detected optical path bundles 14 spatially separated from each other within the brain 12 in a single measurement period, or by using a movable source-detector arrangement, the processor 38 may also localize the fast-neural signal in an x-y plane along the surface of the brain 12, such that a three-dimensional location of the fast-neural signal within the brain 12 is determined. The processor 38 may then perform post-processing on the localized fast-neural signal, e.g., determining the level and location of neural activity within the brain 12 (step 144).

Although the optical measurement system 10 illustrated in FIG. 3 has been described as having a single-mode optical throughput, optical measurement systems may have multi-mode optical fibers. For example, an alternative multimode variation of an embodiment system 10' will now be described with respect to FIG. 10. The optical measurement system 10' is similar to the optical measurement system 10 of FIG. 3, with the exception that it comprises an interferometer 28' that includes a multi-mode sample arm optical fiber 70*g*' between the input port 76*b* and light filter 78, and a multi-mode sample arm optical fiber 70*h*' coupled to the output of the light filter 78. Thus, the neural-encoded signal light 60, non-modulated background light 62, and modulated background light 64 combine and exit the brain 12 as combined multi-mode sample light 66*a*', and the light filter 78 is configured for filtering out the intensity modulated background light 64 from this multi-mode sample light 66*a*' and outputting filtered sample light 66*b*'.

The optical measurement system 10' further differs from the optical measurement system 10 in that the interferometer 28' comprises a free-space optical beam combiner/splitter 80' for receiving the respective filtered multi-mode sample light 66*b*' output by the light filter 78 via an input port 80*a*, receiving probe reference light 58 output by the optical beam splitter 72 at an input port 80*b*, and combining the filtered multi-mode sample light 66*b*' and the probe reference light 58 into two-phased modulated interference 68*a* and 68*b* that are respectively output at output ports 80*c* and 80*d*. Due to power conservation, a four-port network, such as the optical beam combiner/splitter 80', inherently requires the total power entering the input ports 80*a*, 80*b* to be equal to the total power exiting the output ports 80*c*, 8*s*0*d*, and thus, the interference light 68*a* exiting the output port 80*c* will have a nominal phase of 0, and the interference light 68*b* exiting the output port 80*d* will have a nominal phase of Tr.

Further details of four-port free-space optical beam combiner/splitters are set forth in U.S. patent application Ser. No. 15/853,209, entitled "System and Method for Simultaneously Detecting Phase Modulated Optical Signals" (now U.S. Pat. No. 10,016,137), which is expressly incorporated herein by reference. Although not illustrated, the interferometer 28' may include lenses and/or collimators to focus and collimate the filtered multi-mode sample light 66b' output by the optical fiber 70h' and optical fiber 70e onto the input ports 80a, 80b of the optical beam combiner/splitter 80'.

The optical measurement system 10' further differs from the optical measurement system 10 in that the interferometer 28' comprises a free-space balanced detector 30'. The free-space balanced detector 30' is similar to the balanced detector 30 illustrated in FIG. 3 in that it outputs the same electrical signal 82 representative of interference light 68, which does not contain DC components, but only signal-carrying frequency components (i.e., the first frequency components and second frequency components). However, since the interference light 68 is already split into two phase-modulated lights 68a, 68b, and does so in a free-space manner, the balanced detector 30' comprises two optical detectors 31a, 31b for respectively detecting the two phase-modulated interference light 68a, 68b output by the respective output ports 80a, 80b of the optical beam combiner/splitter 80', and outputting respective electrical signals 69a, 69b representative of the interference light 68a, 68b. Each of the detectors 31a, 31b may, e.g., take the form of a very simple and inexpensive single component (e.g., a photodiode). The balanced detector 30' further comprises an arithmetic unit 33 for subtracting the electrical signals 31a, 31b (i.e., the phase-modulated interference light 68a,68b), and outputting the electrical signal 82.

In the same manner described above, the processor 38 is configured for digitizing the electrical signal 84 to create data values respectively comprising the first frequency components (i.e., different frequencies of interest $f_{int}$), analyzing the detected interference light 68, and in particular, the desirable frequency band 86a contained in the electrical signal 84 output by the RF filter 32 (i.e., the data values), and based on this analysis, determining a presence and depth of a fast-neural signal within the brain 12. It should be noted that the optical measurement system 10' illustrated in FIG. 9 has an improved through-put compared to the optical measurement system 10 illustrated in FIG. 3, at the cost of lateral spatial resolution.

Figure 11:
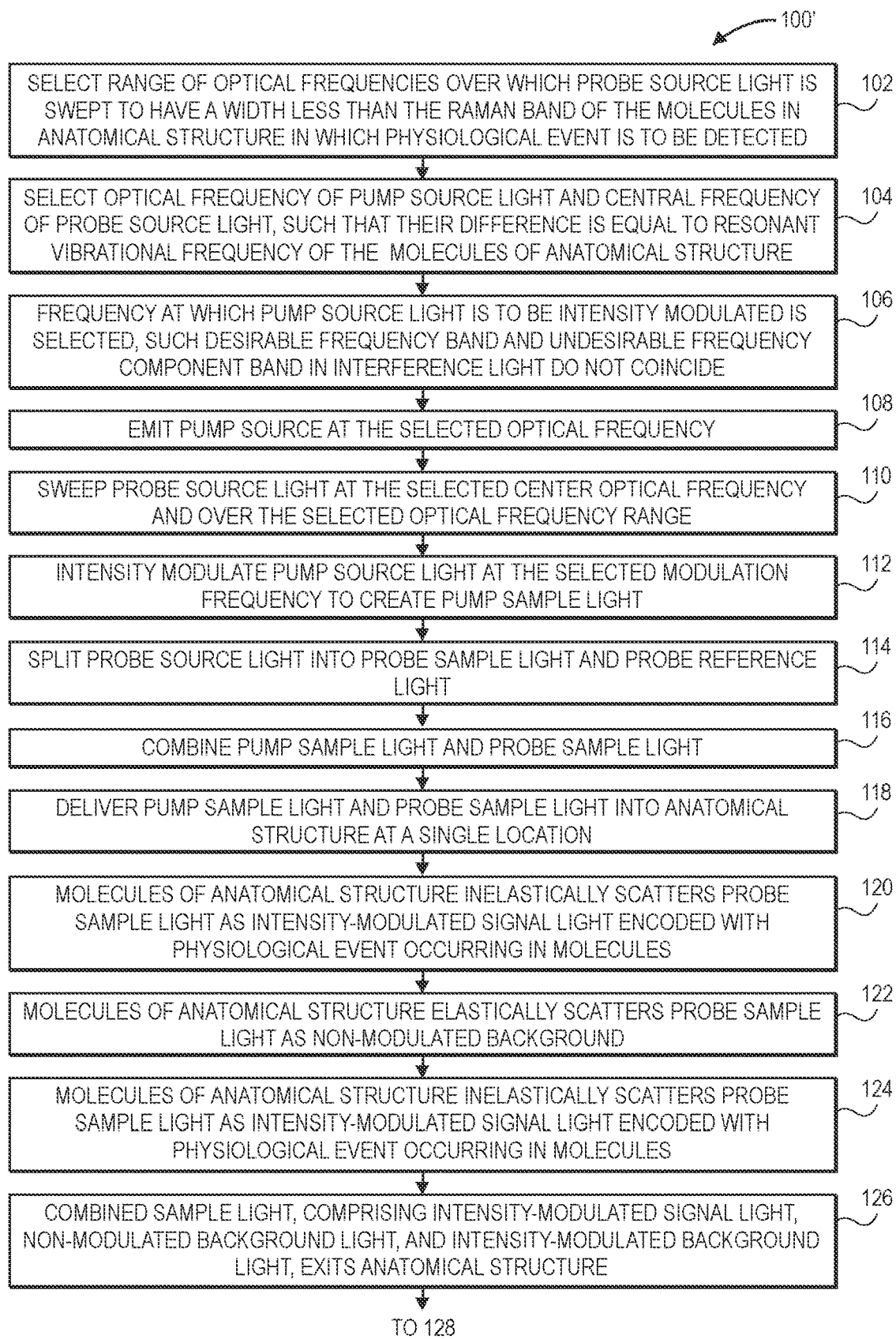
FIG. 11 is a flow diagram illustrating one method used by the optical measurement system of FIG. 10 to non-invasively detect one or more physiological events within an anatomical structure.
Figure 11:
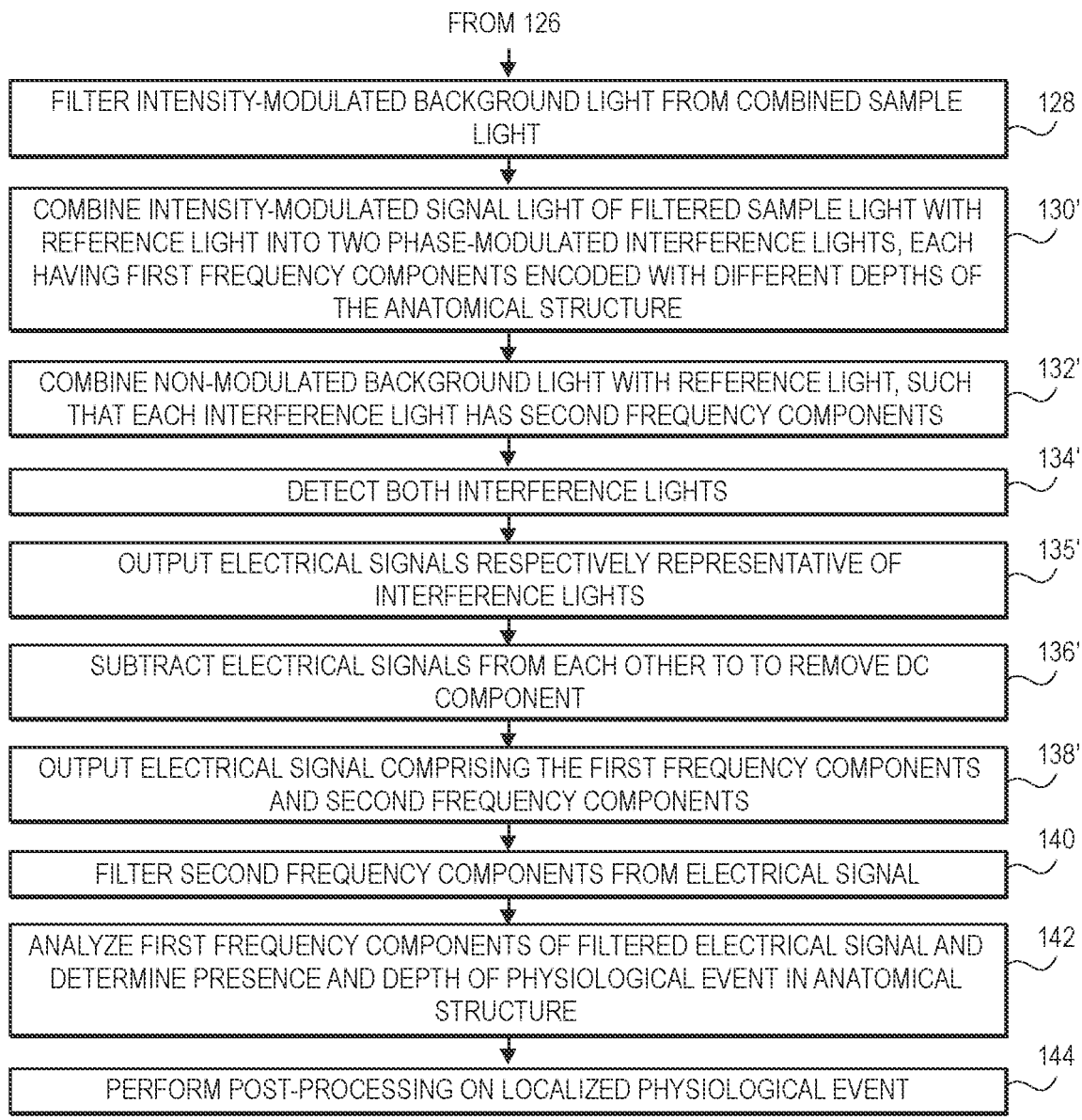

Referring to FIG. 11, having described the structure and function of the optical measurement system 10', one particular method 100' performed by the optical measurement system 10' to non-invasively determine the depth of a physiological event (in this case, a fast-neural signal) in the anatomical structure 12 (in this case, the brain) will now be described. The method 100' is similar to the method 100 described above with respect to FIG. 9, with the exception that the combined sample light 66a' is multi-mode, and two interference lights 68a, 68b are created.

In particular, the interferometer 28' combines (e.g., using the free-space beam combiner 80'), during each of the measurement periods (i.e., each optical wavelength sweep 50), the intensity-modulated signal light 60 of the filtered sample light 66b' and the reference light 58 into two phase-modulated interference lights 68a, 68b (out of phase by 180 degrees), with each interference light 68a, 68b having a first plurality of frequency components encoded with a plurality of different depths of the brain 12 (step 130'), as well as combining the non-modulated background light 62 and the reference light 58, such that each interference light 68a, 68b has a second plurality of frequency components (step 132'). The respective optical detectors 31a, 31b detect the interference lights 68a, 68b (step 134'), and respectively output electrical signals 69a, 69b representative of the interference lights 68a, 68b (step 135'). The arithmetic unit 33 subtracts the electrical signal signals 69a, 69b from each other to remove the DC component (step 136'), and outputs the electrical signal 82 comprising the first plurality of frequency components and second plurality of frequency component (step 138').

In the same manner described above with respect to FIG. 9, the RF filter 32 filters the second frequency components from the electrical signal 82 output by the balanced detector 30' and outputs the electrical signal 84 (step 140), and the processor 38 then analyzes the first frequency components of the electrical signal 84 output by the RF filter 32, and based on this analysis, determines the presence and the depth of the fast-neural signal within the brain 12 (step 142).

Figure 10:
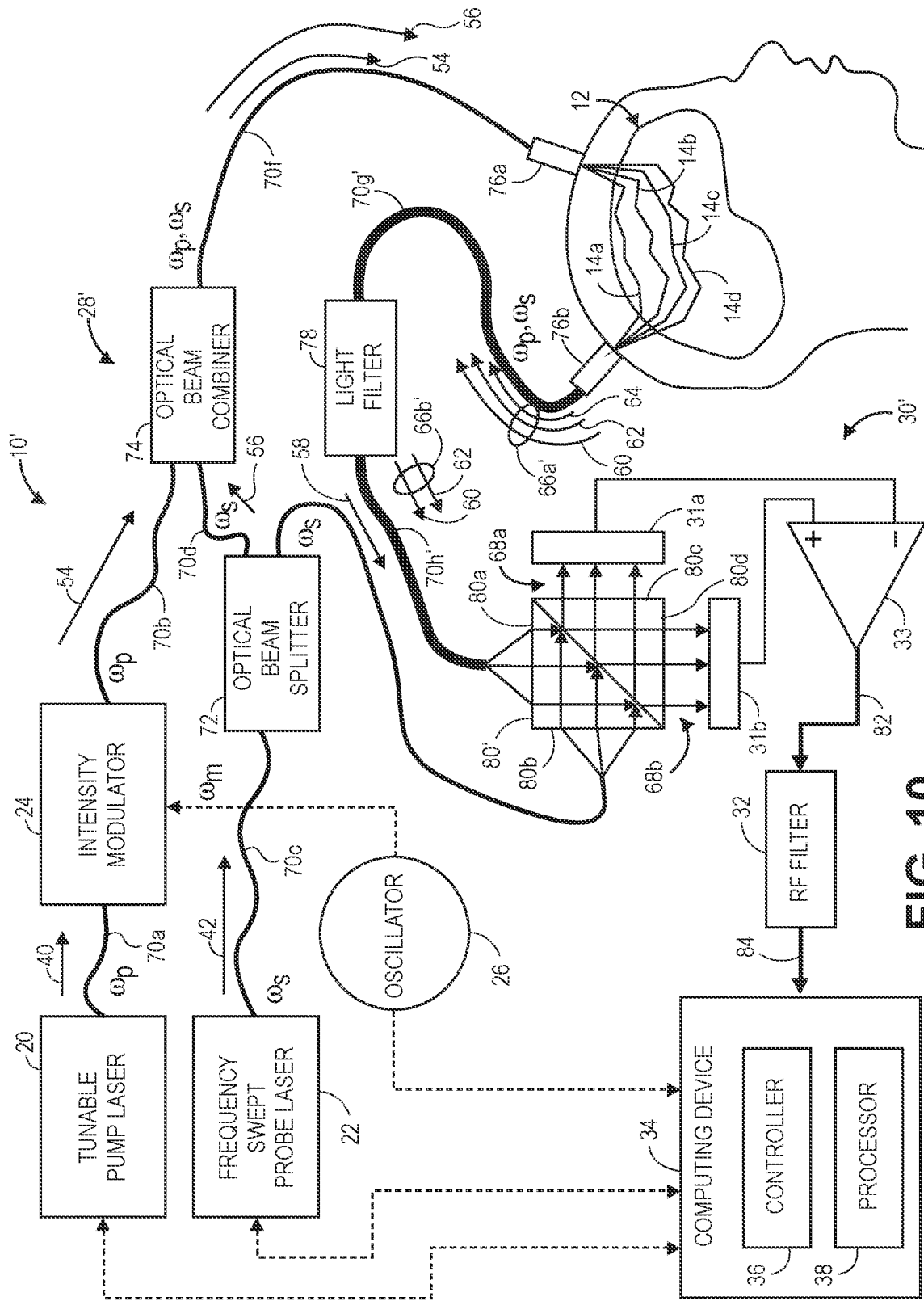
FIG. 10 is a block diagram of an optical measurement system constructed in accordance with another embodiment of the present inventions.
Figure 12:
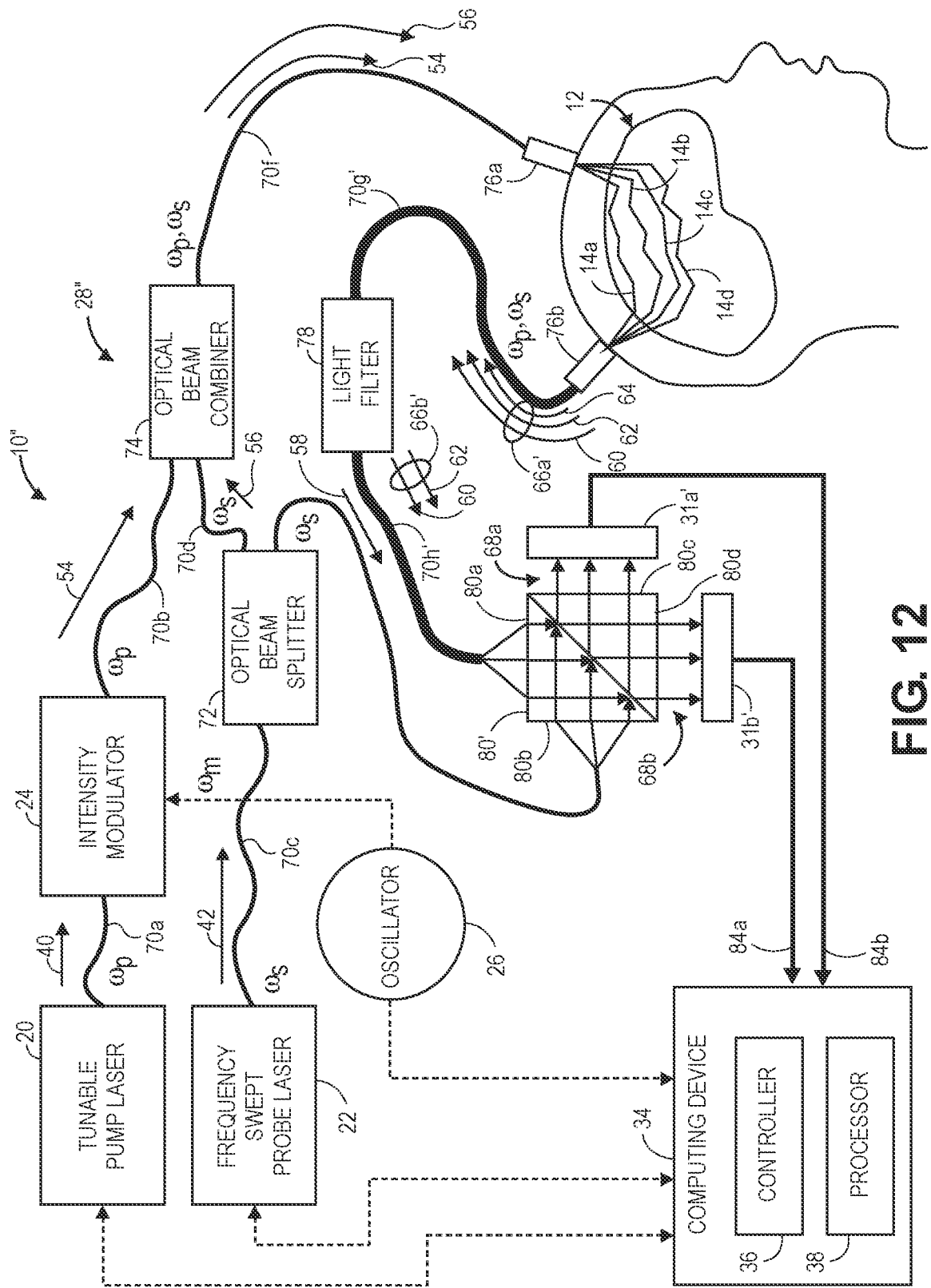
FIG. 12 is a block diagram of an optical measurement system constructed in accordance with still another embodiment of the present inventions.

Although the optical measurement systems 10 and 10' illustrated in FIGS. 3 and 10 have been described as having simple optical detectors and separate frequency filtering devices, one embodiment of an optical measurement system 10" illustrated in FIG. 12 utilizes conventional cameras that both optically detect and filter unwanted frequency components from the interference light.

Figure 13:
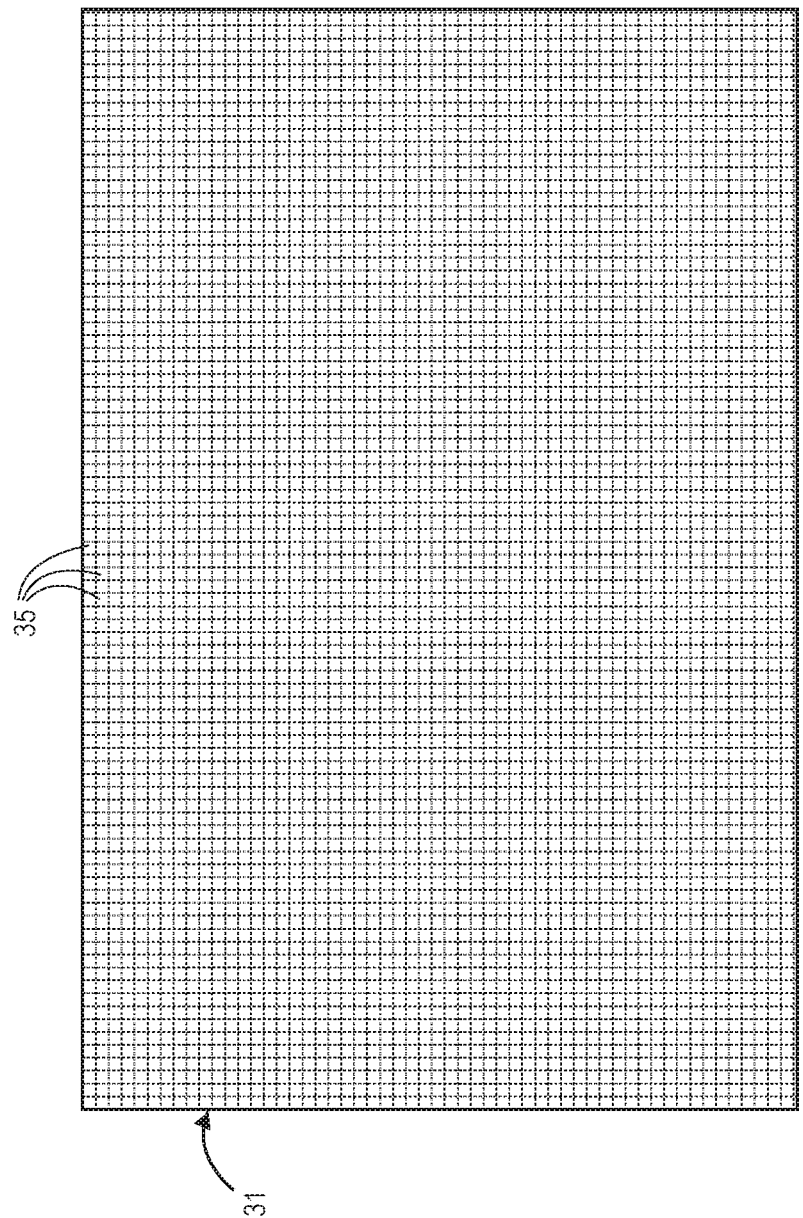
FIG. 13 is a plan view of a conventional camera used in the optical measurement system of FIG. 12.

In particular, the optical measurement system 10" is the same as the optical measurement system 10' of FIG. 10, with the exception that, instead of comprising a balanced detector 30' and RF filter 32, the optical measurement system 10" comprises two optical detector arrays 31a', 31b', each of which comprises an array of detectors or pixels 35, as illustrated in FIG. 13. Each of the optical detector arrays 31a', 31b' is configured for detecting an array of intensity values of an array of spatial components (referred to herein as spatial component intensity values or spatial component intensity value arrays) of the respective interference light 68a, 68b output by the respective output ports 80a, 80b of the optical beam combiner/splitter 80'.

In particular, each of the interference light 68a, 68b, which have been generated from the filtered multi-mode sample light 66b', may be a speckle light pattern, which can be defined as an intensity pattern produced by the mutual interference of a set of scattered wavefronts. That is, a speckle light pattern results from the interference of many waves, but having different phases and amplitudes, which add together to give a resultant wave whose amplitude, and therefore intensity and phase, varies randomly. In this case, the spatial components are speckle grains (approximately the size of a wavelength of the light) of the speckle light pattern 68.

Each of the optical detector arrays 31a', 31b' may be implemented as a conventional camera (e.g., charge coupled device (CCD) camera, a time-of-flight (TOF) imager, such as a MPD, Kinect2, etc.) with a frame rate that can be controlled by the controller 36 in coordination with the optical wavelength sweeps of the probe laser 22. Preferably, the frame rate of the cameras 31a', 31b' is commensurate with the detectable frequency of the physiological event to be detected, and in this case, the fast-neural signal (in the kHz). The optical measurement system 10" can be designed, such that cameras 31a', 31b' filter out all frequency components in the interference light 68a, 68b, except for one frequency of interest $f_{int}$ in the frequency band 86a associated with the contribution of the neural-encoded signal light 60 (i.e., the inelastic scattering of the probe sample light 56 that creates the Raman signal) to the interference light 68a, 68b.

Figure 14:
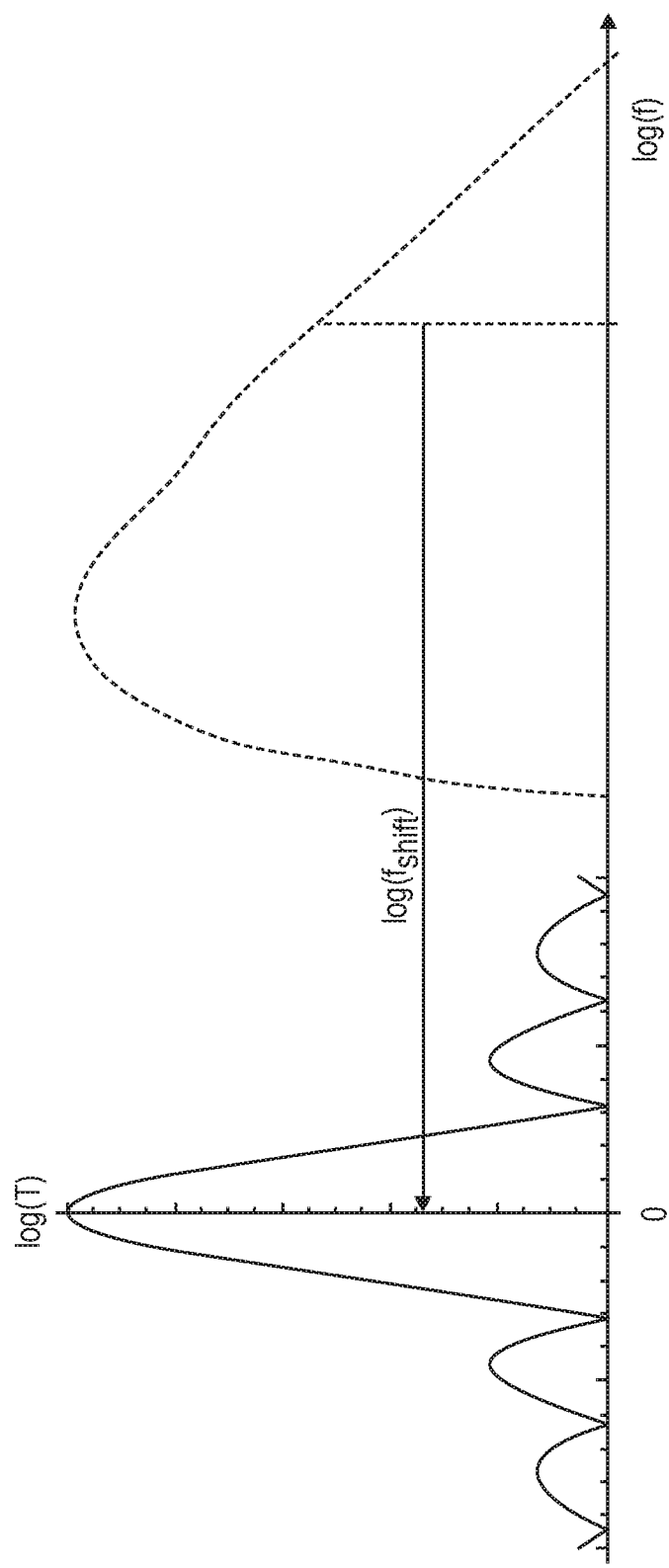
FIG. 14 is a diagram illustrating the low-pass filter transfer characteristics of the conventional camera of FIG. 13.

That is, a conventional camera serves as a low-pass filter with a cutoff frequency of 0 Hz and a transfer characteristic T, as illustrated in FIG. 14. Because a conventional camera integrates a signal over all frequencies, and is most sensitive at 0 Hz, it is desirable that the frequency of interest $f_{int}$ be shifted to 0 Hz in accordance with equation [11], so that the camera is most sensitive at the frequency of interest $f_{int}$. Thus, the modulation frequency $\omega_m$ at which the pump source light 40 is intensity modulated can be varied via the controller 36 (e.g., swept) within a single measurement period or multiple measurement periods to sequentially tune the optical measurement system 10" over time to all of relevant frequencies within the desirable frequency band 86a, thereby enabling detection of a fast-neural signal at various depths in the brain 12.

For any particular frequency of interest $f_{int}$, the cameras 31a', 31b' respectively output sets of electrical signals 84a, 84b corresponding to the detectors or pixels 35 of the respective cameras 31a', 31b'. These two sets of electrical signals 84a, 84b are 180 degrees out of phase, as discussed above, and can be processed (e.g., added or subtracted) by the processor 38 of the computing device 34 to generate data values representative of a singular interference light 68. Each data value, which corresponds to a respective pair of detectors or pixels 35 of the cameras 31a', 31b', not only contains the frequency of interest $f_{int}$ from which the depth of a fast-neural signal can be derived, it also contains a spatial component from which the lateral location of the fast-neural signal can be derived. Thus, the data values contain information associated with both the depth and lateral location of the fast-neural signal. It is noted that the processor 38 need not compute a Fourier transform of any electrical signal, since the electrical signals 84a, 84b only contain the frequency of interest $f_{int}$ detected by the cameras 31a', 31b'.

Figure 15:
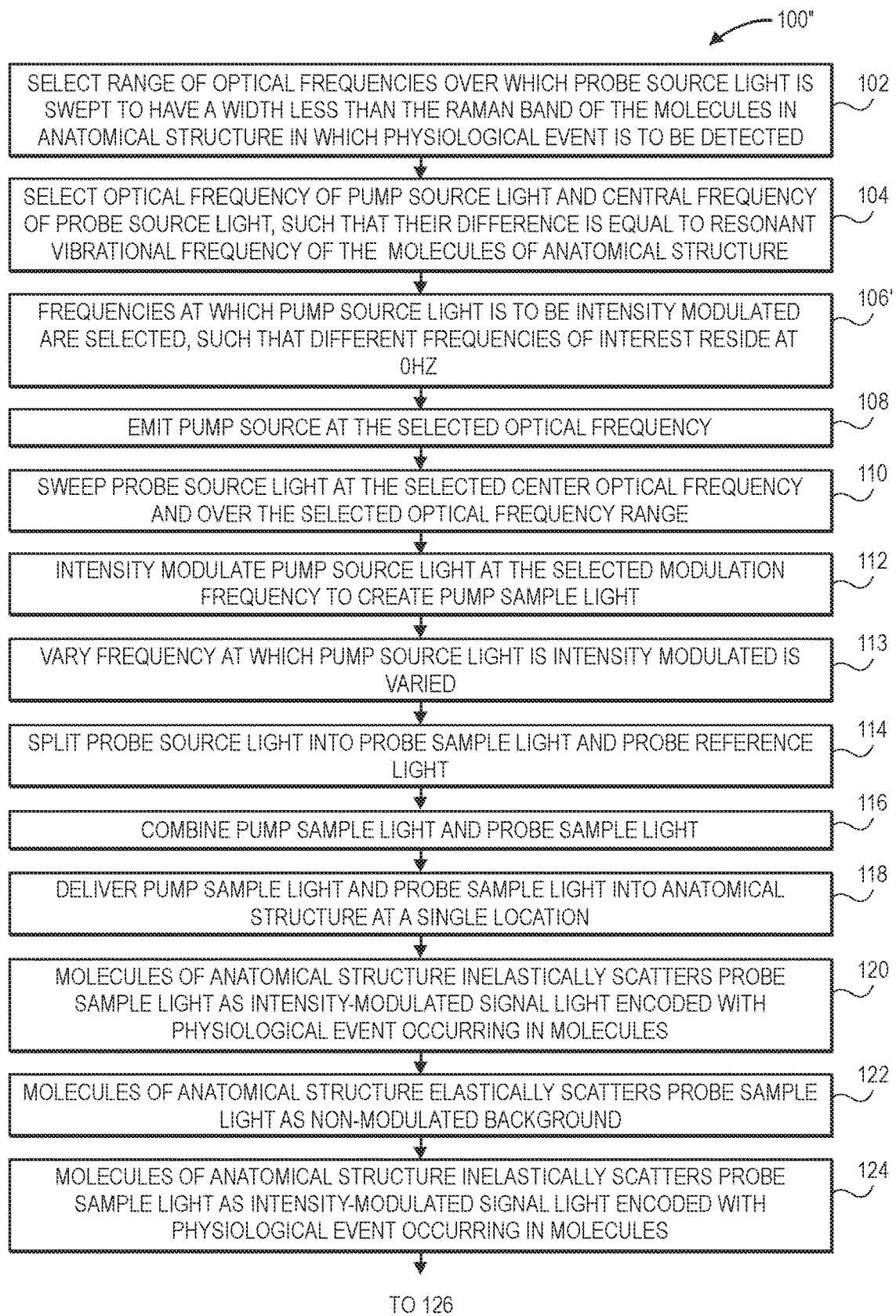
FIG. 15 is a flow diagram illustrating one method used by the optical measurement system of FIG. 12 to non-invasively detect one or more physiological events within an anatomical structure.
Figure 15:
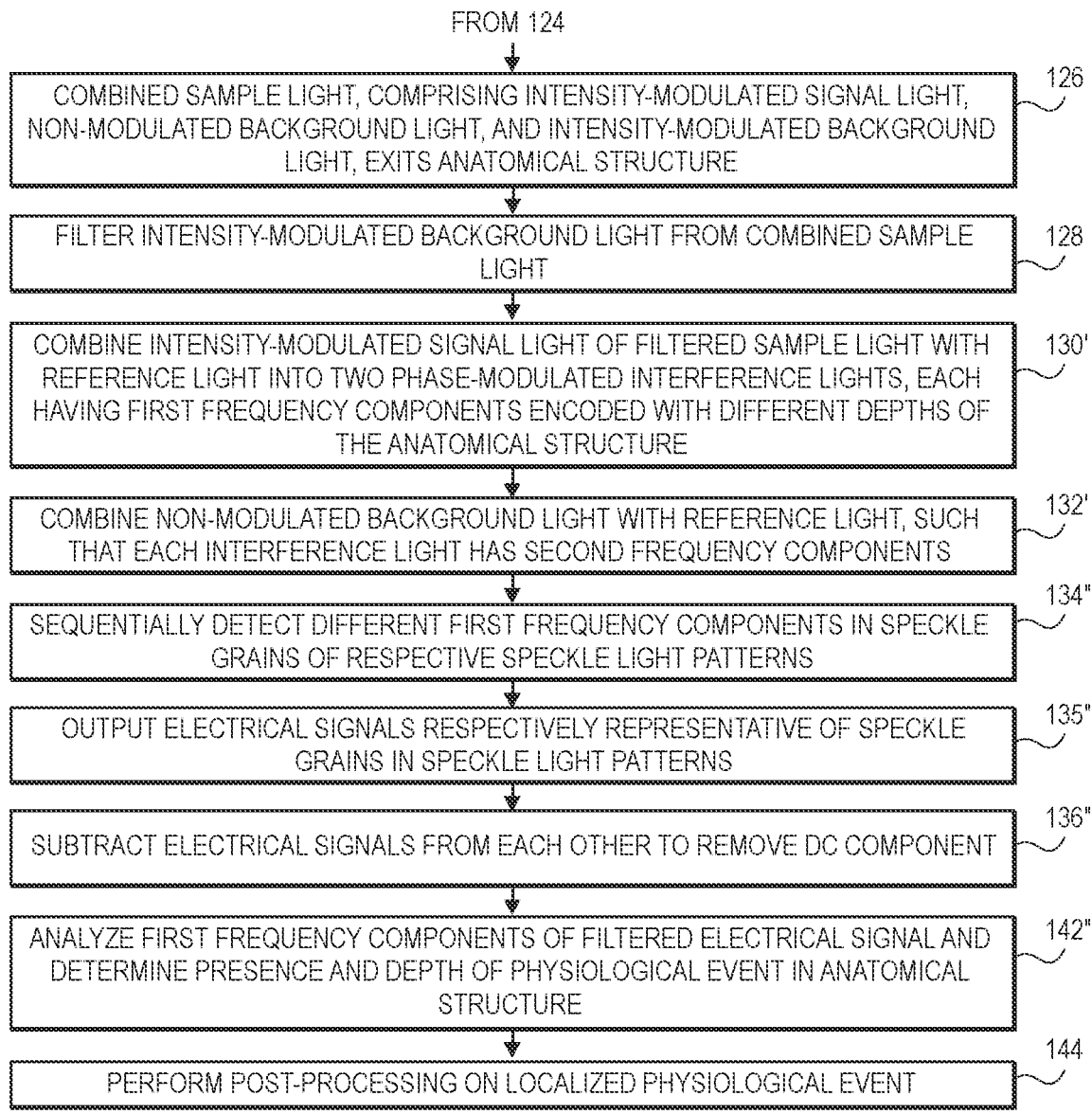

Referring to FIG. 15, having described the structure and function of the optical measurement system 10", one particular method 100" performed by the optical measurement system 10" to non-invasively determine the depth of a physiological event (in this case, a fast-neural signal) in the anatomical structure 12 (in this case, the brain) will now be described.

The method 100" is similar to the method 100' described above with respect to FIG. 9, with the exception that a range of frequencies $\omega_m$ at which the pump source light 40 is to be intensity modulated are selected, such that different desirable frequencies of interest $f_{int}$ in the desirable frequency band 86a reside at 0 Hz (step 106'). As a result, the frequency at which the pump source light 40 is intensity modulated will be varied, such that the cameras 31a', 31b' are most sensitive at the different desirable frequencies of interest $f_{int}$ (step 113).

Thus, instead of detecting all of the first frequency components (i.e., the desirable frequencies of interest $f_{int}$) in the speckle grains of each speckle light patterns 68a, 68b in parallel as was accomplished in step 134' in FIG. 11, the cameras 31a', 31b' sequentially detect the first frequency components in the speckle grains of the respective speckle light patterns 68a, 68b (i.e., as a result of varying the modulation frequency $\omega_m$ of the pump source light 40) (step 134"), and respectively output electrical signals 84a, 84b representative of the speckle light patterns 68a, 68b (step 135"). That is, the cameras 31a', 31b' inherently filter out the frequency components other than one of the first frequency components (i.e., the frequency of interest $f_{int}$) to which the optical measurement system 10" is set (by virtue of selecting the modulation frequency $\omega_m$ of the pump source light 40).

The processor 38 then sequentially processes (for each first frequency component) the resulting detected speckle light patterns 68a, 68b (i.e., by subtracting the two sets of electrical signals 84a, 84b from each other to generate data values representative of a singular interference light 68 without a DC component (step 136"). The processor 38 need not transform the electrical signal 84a, 84b into the frequency domain, and thus, analyzes the first frequency components of the resultant difference between the electrical signals 84a, 84b in the time domain, and based on this analysis, determines the presence and the depth of the fast-neural signal within the brain 12 (step 142").

Figure 16:
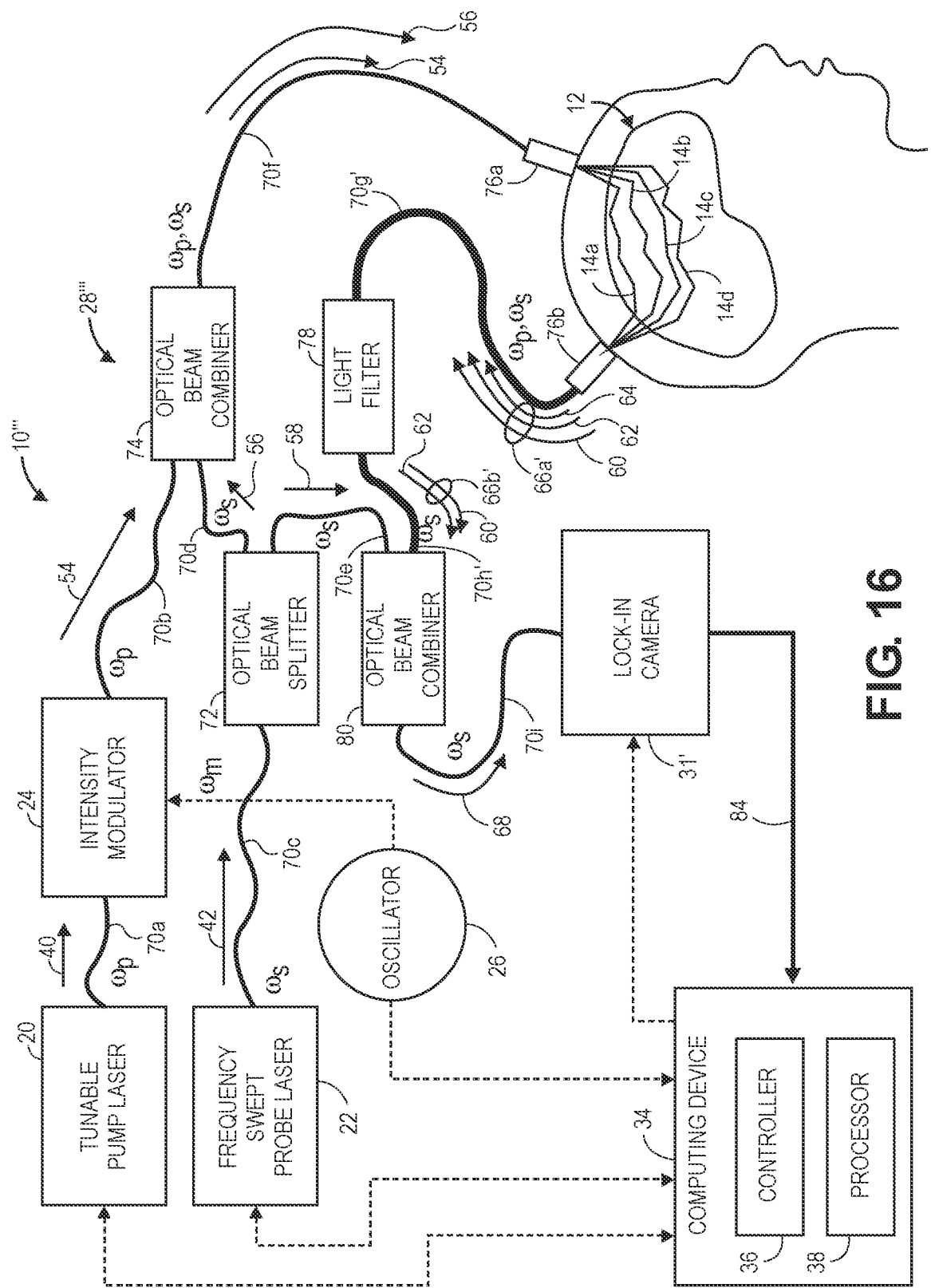
FIG. 16 is a block diagram of an optical measurement system constructed in accordance with yet another embodiment of the present inventions.

Although the optical measurement system 10" illustrated in FIG. 12 has been described as having conventional cameras, one embodiment of an optical measurement system 10" illustrated in FIG. 16 utilizes a single lock-in camera that optically detects and filters unwanted frequency components and the DC signal from the interference light.

In particular, the optical measurement system 10" is the same as the optical measurement system 10" of FIG. 12, with the exception that, instead of comprising an optical beam combiner/splitter 80' and two conventional cameras 31a', 31b', the optical measurement system 10" comprises an interferometer 28" including the optical beam combiner 80 of the optical measurement system 10 of FIG. 2 and a single lock-in camera 31' configured for detecting an array of intensity values of an array of speckle grains of a single speckle light pattern 68 output by the optical beam combiner 80. The lock-in camera 31' is configured for detecting the speckle light pattern 68 output from the optical beam combiner 80, sequentially extracting the first frequency components in the desirable frequency band 86a (i.e., the frequencies of interest $f_{int}$) from the detected speckle light pattern 68, and sequentially outputting an electrical signal 84 containing the first frequency components. Thus, at any particular moment in time, the lock-in camera 31' is capable of selectively locking into a specific frequency component (i.e., the frequency of interest $f_{int}$), as opposed to a conventional camera, which is only capable of locking into 0 Hz.

In general, lock-in cameras include a class of digital cameras in which multiple measurements of a light field are rapidly made at each pixel in a temporally precise fashion synchronized with an external trigger or oscillation and stored in multiple "bins" within each pixel, in contrast with conventional cameras, which store only one value per pixel that merely aggregate the incoming photo-electrons over the camera frame integration time. Lock-in cameras may also perform on-chip computations on the binned values (e.g., using an on-chip field-programmable gate array (FPGA), enabling a portion of the processor 38 to be embodied in the lock-in camera.

Lock-in cameras perform analog lock-in detection while outputting only the information, such as oscillation amplitude and phase shift, on the AC signal component at the temporal frequency to which it is locked. Since the information output by the lock-in camera is only the amplitude or phase shift parameters of a given frequency component, lock-in cameras dramatically increase the bit efficiency of analog to digital conversion by using all the bits to represent only the AC signal of interest. Lock-in cameras also reduce the amount of data to be transferred by transmitting only one frame of the measurement, instead of multiple frames of raw images composed of both the AC signal of interest and background, which may be later digitally processed to extract amplitudes and phases of particular frequency components from the interference light 68.

Thus, at any given time, the electrical signal 84 output by the lock-in camera 31' contains a frequency component in the desirable frequency band 86a that is set by the control signal output by the controller 36. The processor 38 is configured for analyzing the detected interference light 68, and in particular, each frequency component of the desirable frequency band 86a contained in the electrical signal 84 output by the lock-in camera 31', and based on this analysis, determining a presence and depth of a fast-neural signal within the brain 12. It is noted that the processor 38 need not compute a Fourier transform of the electrical signal 84, since the electrical signal 84 only contains the frequency of interest $f_{int}$ extracted by the lock-in camera 38.

Figure 17:
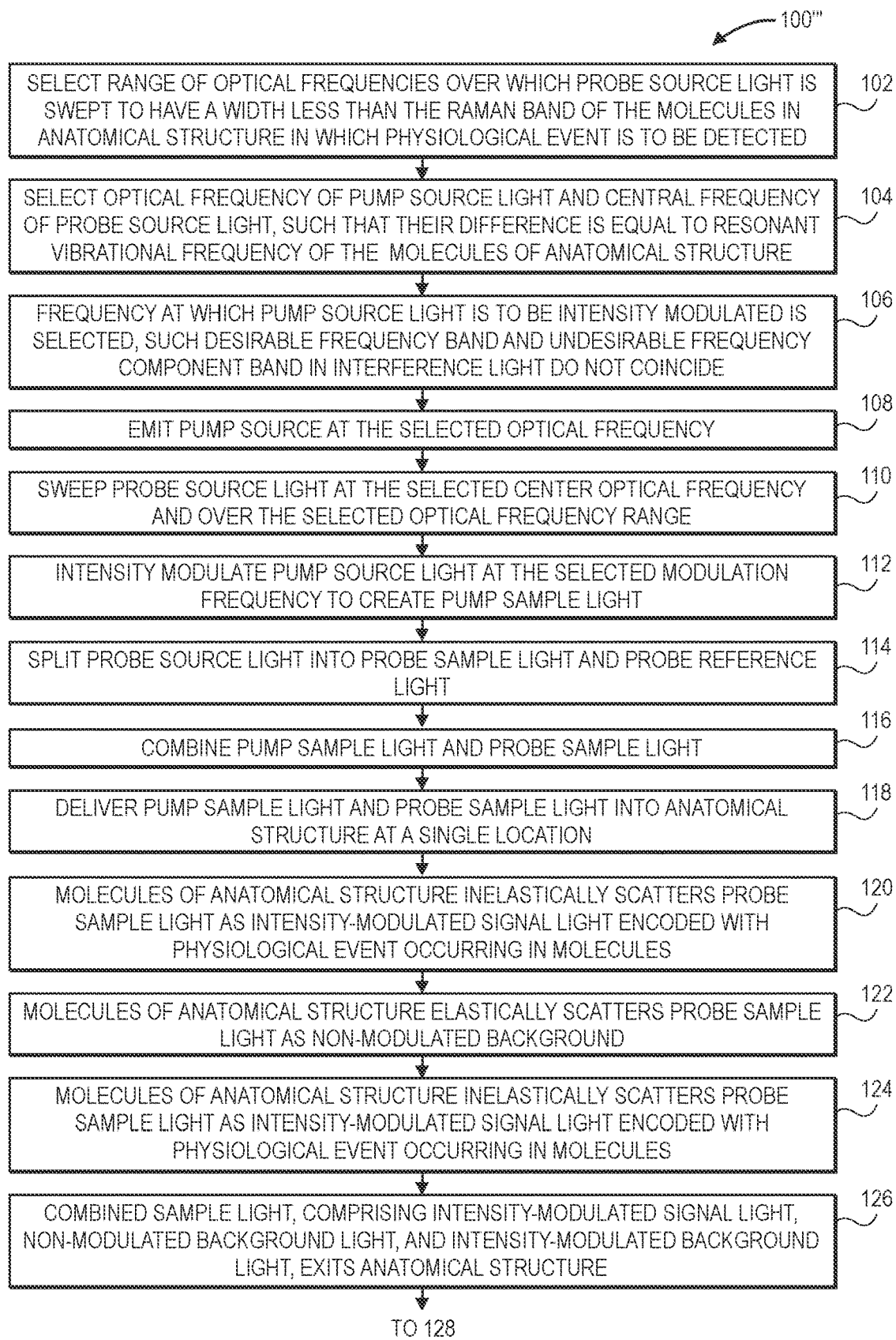
FIG. 17 is a flow diagram illustrating one method used by the optical measurement system of FIG. 16 to non-invasively detect one or more physiological events within an anatomical structure.
Figure 17:
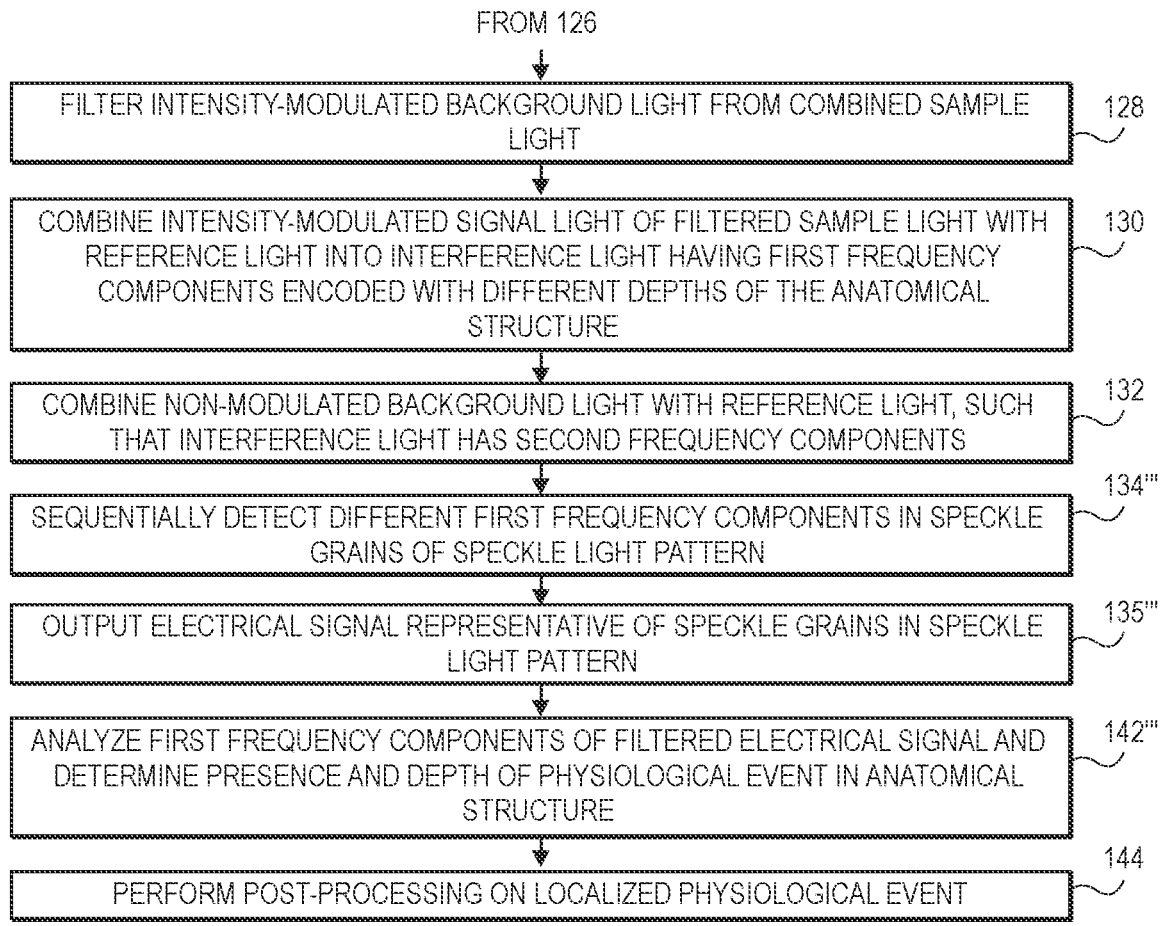

Referring to FIG. 17, having described the structure and function of the optical measurement system 10", one particular method 100" performed by the optical measurement system 10" to non-invasively determine the depth of a physiological event (in this case, a fast-neural signal) in the anatomical structure 12 (in this case, the brain) will now be described.

The method 100" is similar to the method 100" described above with respect to FIG. 15, with the exception that the frequency $\omega_m$ at which the pump source light 40 is intensity modulated is not varied, such that different desirable frequencies of interest $f_{int}$ in the desirable frequency band 86a reside at 0 Hz. Thus, only one frequency $\omega_m$ at which the pump source light 40 is intensity modulated needs to be selected (step 106). Despite the fact that the only one frequency $\omega_m$ at which the pump source light 40 is intensity modulated (step 112), the lock-in camera 31' sequentially detects the first frequency components (i.e., the desirable frequencies of interest $f_{int}$) in the speckle grains of a single speckle light pattern 68 in response to control signals from the controller 36 (step 134"), and respectively digitally outputs an electrical signal 84 representative of the speckle light pattern 68 (step 135"). The processor 38 need not transform the electrical signal 84a, 84b into the frequency domain, and thus, analyzes the first frequency components of the resultant difference between the electrical signals 84a, 84b in the time domain, and based on this analysis, determines the presence and the depth of the fast-neural signal within the brain 12 (step 142").

Figure 18:
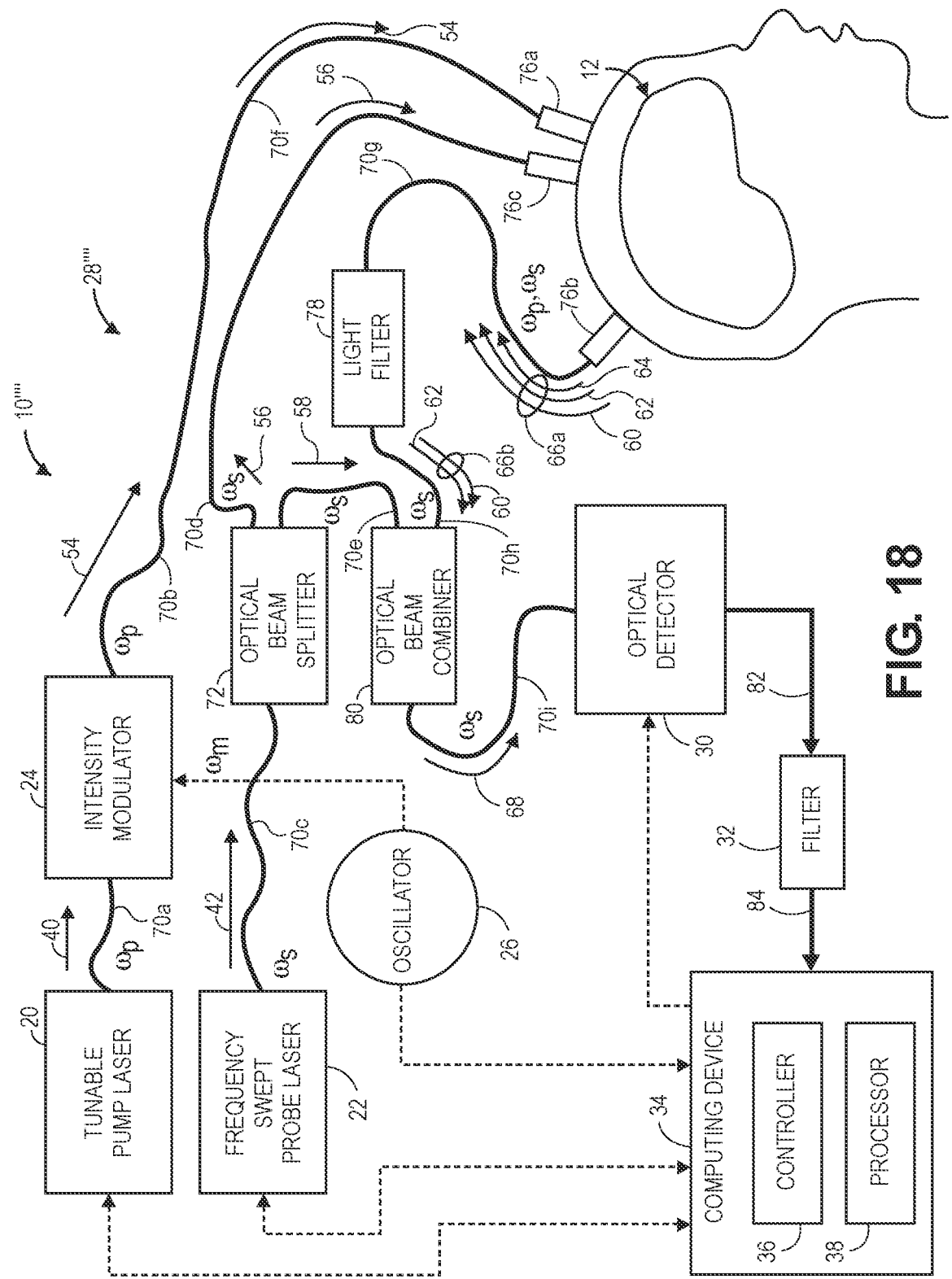
FIG. 18 is a block diagram of an optical measurement system constructed in accordance with yet another embodiment of the present inventions.

Although the interferometers of the optical measurement systems 10, 10', 10", and 10''' are illustrated in FIGS. 3, 10, 12, and 16 as having a single output port 76a for delivering the pump sample light 54 and probe sample light 56 into the brain 12 (in effect, combining the pump sample light 54 and probe sample light 56 via the optical beam combiner 74 prior to delivery into the brain 12), one embodiment of an optical measurement system 10"" illustrated in FIG. 18 comprises an interferometer 28"" that includes two output ports 76a, 76c for respectively delivering the pump sample light 54 and probe sample light 56 into the brain 12, with the input port 76b continuing to receive the combined sample light 66 from the brain 12. Thus, the pump sample light 54 and probe sample light 56 are not combined via an optical beam combiner prior to delivery into the brain 12, but rather are combined within the brain 12 subsequent to their delivery into the brain 12. Although the optical measurement system 10"" is described herein as having the optical beam combiner 80, optical detector 30, and RF filter 32 of the optical measurement system 10 of FIG. 3, it should be appreciated that the optical measurement system 10"" can be modified to include any of the additional or alternative components of the optical measurement systems 10', 10", and 10''' of FIGS. 10, 12, and 16.

Figure 19:
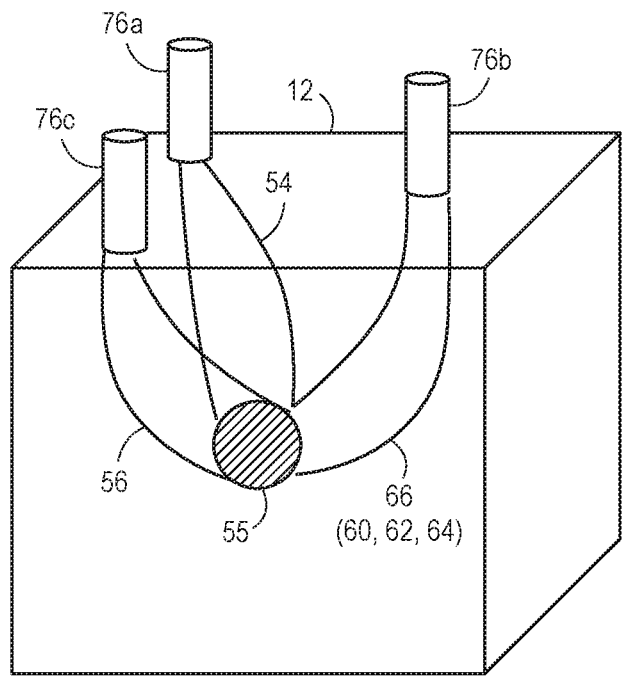
FIG. 19 is a plan view illustrating a confined sensitivity in the anatomical structure created by the optical measurement system of FIG. 18.

In the same manner described above with respect to the optical measurement system 10 in FIG. 3, a portion of the probe sample light 56 is inelastically scattered by the brain 12 as physiological-encoded (in this case, neural-encoded) signal light 60 (i.e., the Raman signal) at the optical frequency $\omega_s$ and intensity modulated at the modulation frequency $\omega_m$ of the intensity modulated pump sample light 54, a portion of the probe sample light 56 is elastically scattered by the brain 12 as non-modulated background light 62 at the at the optical frequency $\omega_s$, and a portion of the pump sample light 54 is scattered (elastically and inelastically) by the brain 12 as background light 64 intensity modulated at the modulation frequency $\omega_m$ of the intensity modulated pump sample light 54. The neural-encoded signal light 60, non-modulated background light 62, and modulated background light 64 combine and exit the brain 12 as combined sample light 66, as illustrated in FIG. 19. However, unlike the optical measurement system 10, because the pump sample light 54 and probe sample light 56 enter the brain 12 at two different locations that are relatively far apart from each other, their intersection in the brain 12 with the combined sample light 66 that is received by the input port 76b creates a confined sensing zone 55 within the brain 12, thereby providing the optical measurement system 10"" with an enhanced lateral resolution.

Figure 20:
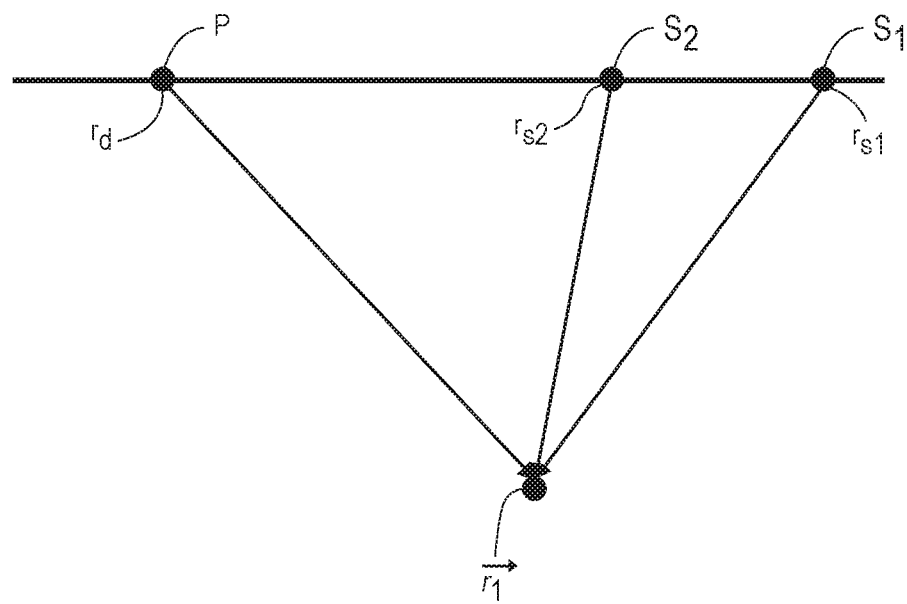
FIG. 20 is a diagram illustrating the calculation of the spatial sensitivity of the optical measurement system of FIG. 18.

Referring to FIG. 20, the spatial resolution of the optical measurement system 10"" can be calculated for an infinitely large turbid medium by first calculating the photon fluence $\varphi(r)$ (defined as the number of photons per area moving radially outward from the infinitesimal volume at position r). The change in fluence detected at position $r_d$ (i.e., the location of the input port 76b) can be given as:

$$\varphi(r_d) = \varphi_0(r_d) - q\alpha_1(r_d, r_1), \qquad [12]$$

where $\varphi_0(r_d)$ is the nominal photon fluence (without a Raman signal) detected at position $r_d$, $\varphi_1(r_d, r_1)$ is the photon fluence (with a Raman signal) detected at position $r_d$ given a source at position $\vec{r}_1$, and q is the change in the photon fluence (with a Raman signal) detected at position $r_d$ given a source at position $\vec{r}_1$ in response to a disturbance (e.g., a fast-neural signal) at position $r_d$.

Assuming that $\varphi_0(r_d)$ is the total fluence sourced at position $r_{s1}$, and $\varphi_1(r_d, r_1)$ is the fluence sourced at position $r_{s1}$ and position $r_{s2}$ that both pass through position $\vec{r}_1$, the frequency domain diffusion equations for $\varphi_0(r_d)$ and $\varphi_1(r_d, r_1)$ can be respectively given as:

$$\varphi_0(r_d) = \frac{1}{4\pi D} \frac{s_1 v e^{-(k|r_d - r_{s1}|)}}{|r_d - r_{s1}|}, \qquad [13]$$

$$\alpha_1(r_d, r_1) = \frac{1}{4\pi D} \frac{s_1 v e^{-(k|r_1 - r_{s1}|)}}{|r_1 - r_{s1}|} \times \frac{s_2 v e^{-(k|r_1 - r_{s2}|)}}{|r_1 - r_{s2}|} \times \frac{v e^{-(k|r_1 - r_d|)}}{|r_1 - r_d|}, \qquad [14]$$

where v is the speed of light in tissue, $\alpha$ is the fraction of dynamic photon scattering events in tissue, k is the wavevector, $s_1$ is the intensity of the pump sample light 54, $s_2$ is the intensity of the probe sample light 56, $r_d$ is the point at which the combined sample light 66 exits the brain 12, and $\vec{r}_1$ is the position at which the pump sample light 54 and probe sample light 56 intersect.

Assuming that we look at the intensity change due to the existence of a Raman signal, we have:

$$\varphi(r_d) = \varphi_0(r_d)\left[1 - \frac{q\alpha_1(r_d, r_1)}{\varphi_0}\right] = \varphi_0[1 - qP(r_d, r_1)]. \quad [15]$$

The spatial sensitivity can then be calculated as:

$$P(r_d, r_1) = \frac{\frac{S_2}{4\pi D} \times \{-k[|r_1 - r_{s1}| + |r_1 - r_{s2}| + |r_1 - r_d| - |r_d - r_{s1}|]\}}{\frac{|r_1 - r_{s1}||r_1 - r_{s2}||r_1 - r_d|}{|r_d - r_{s1}|}} \quad [16]$$

Equation [16] assumes that the intensity change occurs at a point. If it is assumed that the intensity change occurs in a volume, then the integral of the volume around position $\vec{r}_1$ can be computed. Assuming a semi-infinitely large turbid medium, a scattering coefficient of approximately 1 mm$^{-1}$, an absorption coefficient of 0.02 mm$^{-1}$, and a 60 mm separation between the positions of the ports 76a-76c, the peak sensitivity of the sensing zone 55 can be computed to be 9 mm below the surface, and have a full-width at half-wave (FWHM) of about 4 mm in depth, and a lateral dimension of 10 mm. It should be appreciated that one of ordinary skill in the art can replace the infinite model described above with a semi-infinite, slab, parallel-piped, or any other model.

Although the approach set forth above assumes a continuous wave (CW) pump source light 40 and a CW probe source light 42 (or at least pulsed wave (PW) pump source light 40 and a PW probe source light 42 have a duration greater than the measurement period), the pump source 40 and probe source light 42 can alternatively take the form of very short pulses (e.g., in the range of 0.1 ns-1.0 ns) to increase the spatial resolution (at the cost of reduced signal intensity). By controlling the timing between the onset of the pulse of the resulting pump sample light 54, the onset of the resulting probe sample light 56, and the gated detection of the combined sample light 66 relative to each other, the position of the sensing zone 55 may be controllably shifted without physically displacing any of the ports 76a-76c.

Figure 21:
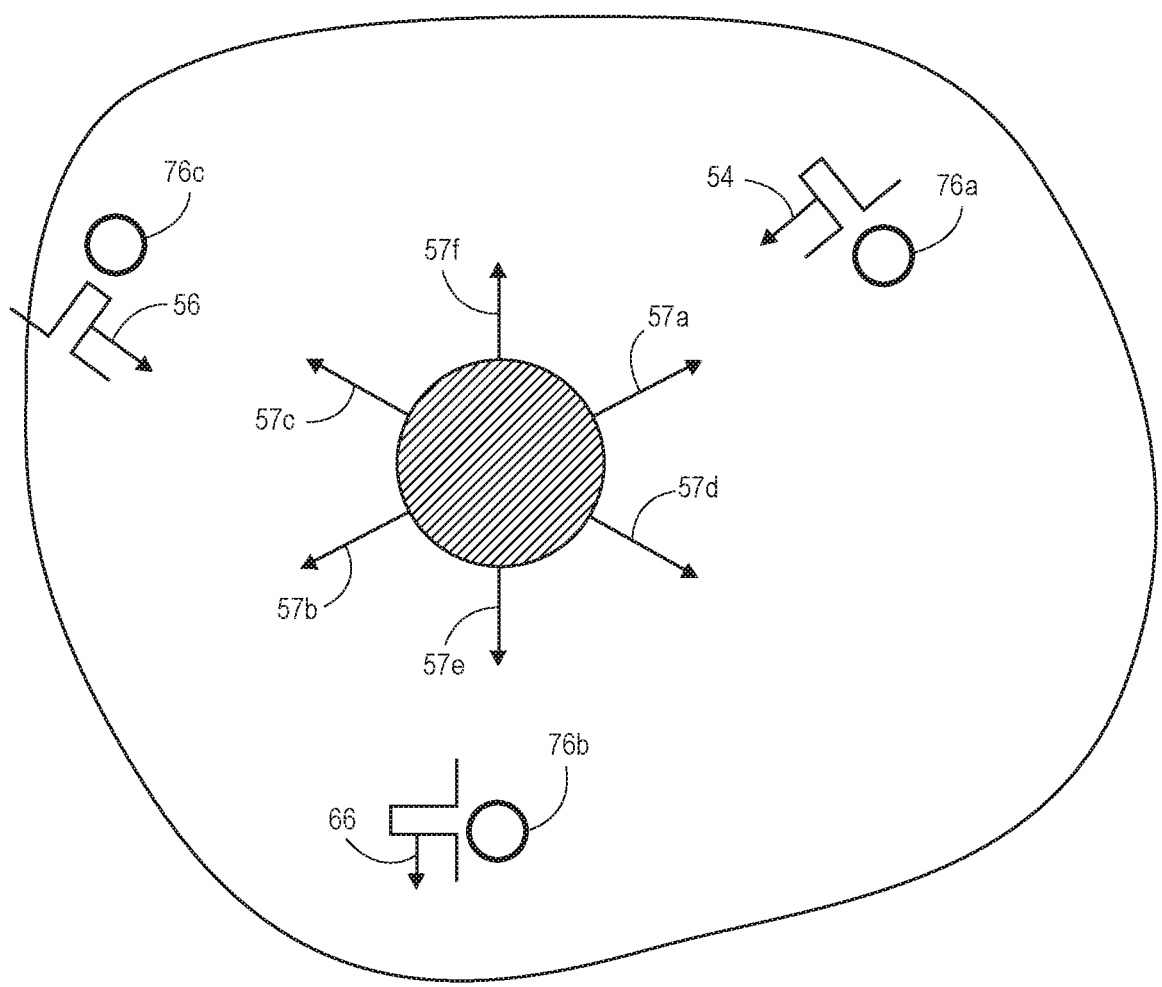
FIG. 21 is a diagram illustrating one technique for displacing a sensitivity zone using a pulsed version of the optical measurement system of FIG. 18.

In particular, referring to FIG. 21, the sensing zone 55 between the ports 76a-76c may be laterally shifted in any direction by varying at least one of the onsets of the pulsed pump sample light 54 and pulsed probe sample light 56 and gated detection of the pulsed sample light 66. For example, if the onset of the pulsed pump sample light 54 is earlier, the sensing zone 55 will move towards the port 76a in the direction 57a; if the onset of the pulsed pump sample light 54 is later, the sensing zone 55 will move away from the port 76a in the direction 57b; if the onset of the pulsed probe sample light 56 is earlier, the sensing zone 55 will move towards the port 76c in the direction 57c; if the onset of the pulsed probe sample light 56 is later, the sensing zone 55 will move away from the port 76c in the direction 57d; if the detection gating of the pulsed sample light 66 is later, the sensing zone 55 will move towards the port 76b in the direction 57e; and if the detection gating of the pulsed sample light 66 is earlier, the sensing zone 55 will move away from the port 76b in the direction 57f. It should be appreciated that any combination of the onsets of the pulsed pump sample light 54 and pulsed probe sample light 56 and gated detection of the pulsed sample light 66 can be controlled, to displace the sensing zone 55 to any point on a surface defined by the ports 76a-76c.

Figure 22:
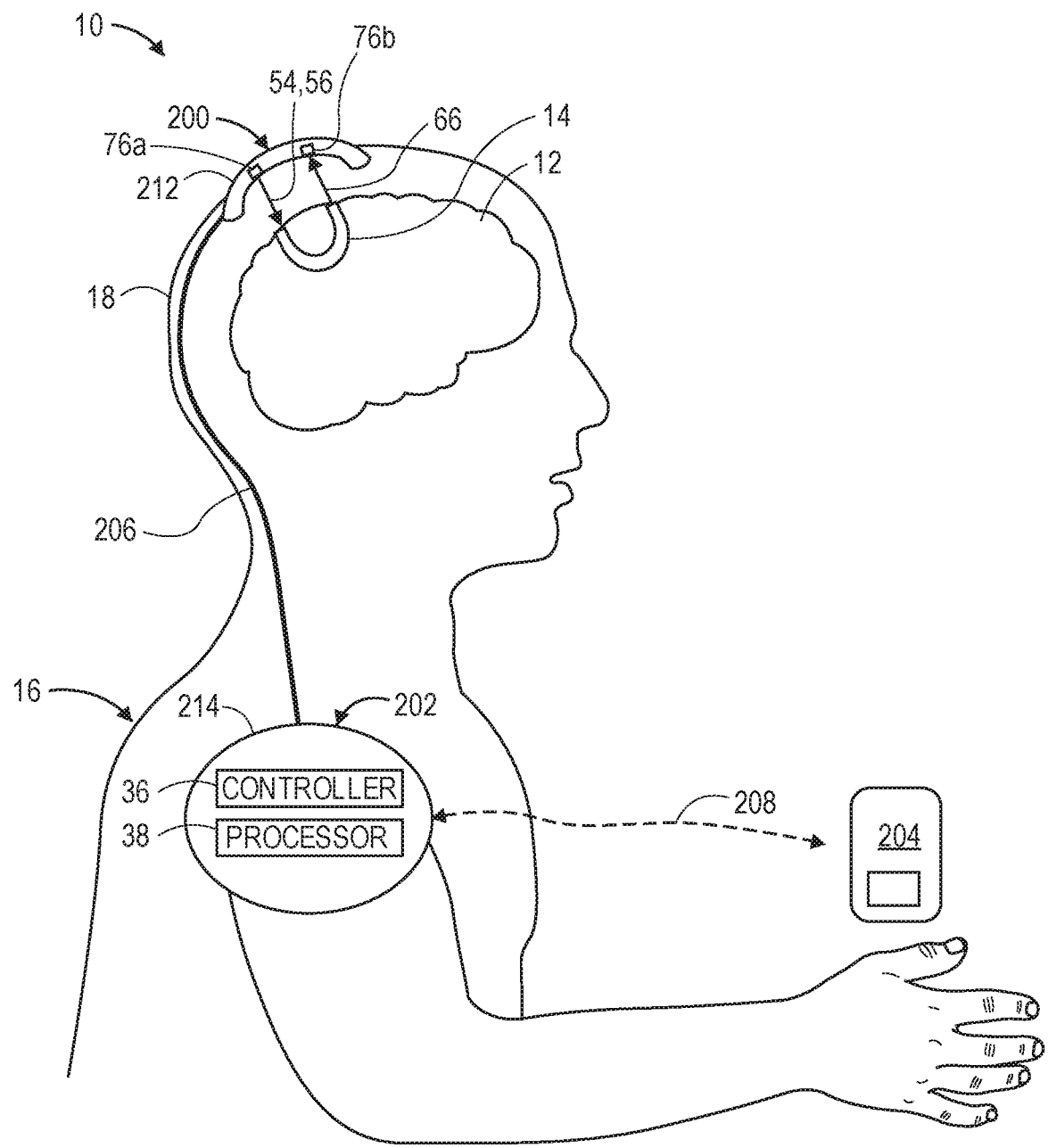
FIG. 22 is a plan view of a physical implementation of the optical measurement systems described herein.

Referring now to FIG. 22, the physical implementation of the optical measurement system 10 (and alternatively, the optical measurement systems 10', 10", 10''', and 10'''') for use in localizing a fast-neural signal within the brain 12 of a user 16 will be described. The optical measurement system 10 includes a wearable unit 200 that is configured for being applied to the user 16, and in this case, worn on the head 18 of the user 16; an auxiliary head-worn or non-head-worn unit 202 (e.g., worn on the neck, shoulders, chest, or arm) coupled to the wearable unit 200 via a wired connection 206 (e.g., electrical wires); and an optional remote processor 204 in communication with the patient-wearable auxiliary unit 202 coupled via a wired connection 208 (e.g., electrical wires). Alternatively, the optical measurement system 10 may use a non-wired connection (e.g., wireless radio frequency (RF) signals (e.g., Bluetooth, Wifi, cellular, etc.) or optical links (e.g., fiber optic or infrared (IR)) for providing power to or communicating between the respective wearable unit 200 and the auxiliary unit 202, and/or a wired connection between the auxiliary unit 202 and the remote processor 204.

The wearable unit 200 comprises the pump laser 20, probe laser 22, intensity modulator 24, interferometer 28 (along with the output port 76a (and in the case of the optical measurement system 10''', output ports 76a and 76c) for delivering the pump sample light 54 and probe sample light 56 generated by the respective pump laser 20 and probe laser 22 into the head 18 of the user 16, and the input port 76b for receiving the combined sample light 66 from the head 18 of the user 16), and the optical detector 30 (all illustrated in FIG. 3), or alternatively the optical detectors 31a, 31b (illustrated in FIG. 10), cameras 31a', 31b' (illustrated in FIG. 12), or camera 31' (illustrated in FIG. 16), as well as a support structure 212 containing the pump laser 20, probe laser 22, intensity modulator 24, interferometer 28, and optical detector 30.

The auxiliary unit 202 comprises the computing device 34 (including the controller 36 and processor 38), as well as the oscillator 26 and RF filter 32 (all illustrated in FIGS. 3 and 10). The auxiliary unit 202 further comprises a housing 214 containing the controller 36 and processor 38. The controller 36 is configured for controlling the operational functions of the wearable unit 200, whereas the processor 38 is configured for processing the electrical signal 84 by the optical detector RF filter 32 (i.e., the interference light 68) acquired by the wearable unit 200 to identify and localize the fast-neural signal within the brain 12. The auxiliary unit 202 may additionally include a power supply (which if head-worn, may take the form of a rechargeable or non-chargeable battery), a control panel with input/output functions, a display, and memory. Alternatively, power may be provided to the auxiliary unit 202 wirelessly (e.g., by induction). The remote processor 204 may store data from previous sessions, and include a display screen.

As better illustrated in FIGS. 23A and 23B, the wearable unit 200 is configured for being placed adjacent to the head 18 of the user 16 and emitting the pump sample light 54 and probe sample light 56 into the brain 12, where it scatters, resulting in the neural-encoded combined sample light 66 that exits the brain 12. In particular, the pump sample light 54 and probe sample light 56 first passes through the scalp 216a, skull 216b, and cerebral spinal fluid (CSF) 216c along a relatively straight path, enters the brain 12, then exits as the combined sample light 66 through the CSF 216c, skull 216b, and scalp 216a, thereby defining a banana-shaped bundle of optical paths 14 (14a-14d in FIG. 3). The wearable unit 200 may alternatively, by adding additional optical source-detector pairs, create multiple spatially separated detected bundle of optical paths 14 along which the light may propagate to enable x-y spatial localization of the fast-neural signal.

Referring back to FIG. 22, the support structure 212 may be shaped, e.g., have a banana, headband or hat shape (e.g., helmet, hood, cap, beanie, etc.), or other shape adjustable to the head 18, such that the ports 76a, 76b are in close contact with the outer skin of the head 18, and in this case, the scalp of the user 16. In an alternative embodiment, optical fibers (not shown) may be respectively extended from the ports 76a, 76b, thereby freeing up the requirement that the ports 76a, 76b be disposed in close proximity to the surface of the head 18. In any event, an index matching fluid may be used to reduce reflection of the light generated by the wearable unit 200 from the outer skin of the scalp. An adhesive or belt (not shown) may alternatively be used to secure the support structure 212 to the head 18 of the user 16.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An optical measurement system, comprising:
   a pump optical source configured for generating pump source light having a first optical frequency;
   a probe optical source configured for sequentially generating probe source light over a range of second optical frequencies;
   an optical modulator configured for intensity modulating the pump source light at a modulation frequency;
   an interferometer configured for:
      splitting the intensity modulated probe source light into probe sample light and probe reference light;
      delivering the intensity modulated pump source light as intensity modulated pump sample light, and the probe sample light, into an anatomical structure comprising molecules having a resonant vibrational frequency equal to the difference between the first optical frequency and one of the range of second optical frequencies, whereby a portion of the probe sample light is inelastically scattered by the molecules as signal light intensity modulated at the modulation frequency and encoded with a physiological event occurring in the molecules, a portion of the probe sample light is elastically scattered by the anatomical structure as non-modulated background light, and a portion of the pump sample light is scattered by the anatomical structure as intensity-modulated background light at the modulation frequency, and whereby sample light comprising the intensity modulated signal light, the non-modulated background light, and the intensity-modulated background light exits the anatomical structure;
      filtering the intensity-modulated background light from the exiting sample light; and
      combining the intensity modulated signal light and non-modulated background light of the filtered sample light and the reference light into interference light having a first plurality of frequency components and a second plurality of frequency components displaced from the first plurality of frequency components, each of the first plurality of frequency components being encoded with a physiological event at a different depth of the anatomical structure;
   an optical detector configured for detecting the interference light and outputting an electrical signal comprising the first plurality of frequency components; and
   a processor configured for analyzing the first plurality of frequency components in the electrical signal, and, based on this analysis, determining a presence and a depth of the physiological event in the anatomical structure.

2. The optical measurement system of claim 1, wherein each of the pump source light and the probe source light is continuous wave (CW) light.

3. The optical measurement system of claim 1, wherein the probe optical source has a coherence length equal to or less than 1 cm.

4. The optical measurement system of claim 1, wherein the anatomical structure is a brain.

5. The optical measurement system of claim 4, wherein the physiological event is indicative of neural activity.

6. The optical measurement system of claim 5, wherein the physiological event is a fast-neural signal.

7. The optical measurement system of claim 6, wherein the molecules are neural membrane proteins.

8. The optical measurement system of claim 1, wherein the probe optical source is configured for sequentially generating the probe source light over a range of second optical frequencies by sweeping the probe source light over the range of second optical frequencies.

9. The optical measurement system of claim 1, wherein the range of second optical frequencies has a width less than a bandwidth of a Raman band of the molecules.

10. The optical measurement system of claim 9, wherein a difference between the first optical frequency and a central optical frequency of the range of second optical frequencies coincides with a center of the Raman band of the molecules.

11. The optical measurement system of claim 1, wherein the pump optical source is a tunable optical source.

12. The optical measurement system of claim 1, wherein the electrical signal comprises the first plurality of frequency components and the second plurality of frequency components, the optical measurement system further comprising a filter configured for filtering the second plurality of frequency components from the electrical signal.

13. The optical measurement system of claim 1, further comprising an oscillator configured for generating an oscillating signal at the modulation frequency, wherein the modulator is configured for intensity modulating the pump source light in response to the oscillating signal.

14. The optical measurement system of claim 1, further comprising an optical beam combiner configured for combining the pump sample light and the probe sample light, wherein the interferometer is configured for delivering the combined pump sample light and probe sample light into the anatomical structure at a single location.

15. The optical measurement system of claim 1, wherein the interferometer is configured for respectively delivering the pump sample light and the probe sample light into the anatomical structure at different locations.

16. The optical measurement system of claim 1, wherein the optical detector comprises a balanced detector.

17. The optical measurement system of claim 1, wherein the interference light comprises a speckle interference pattern having a plurality of speckle grains, and wherein the optical detector comprises a camera having an array of pixels configured for respectively detecting the speckle grains.

18. The optical measurement system of claim 1, wherein the optical detector is configured for simultaneously detecting the first plurality of frequency components in the interference light.

19. The optical measurement system of claim 18, wherein the processor is configured for transforming the electrical signal from a time domain into a frequency domain, and analyzing the electrical signal in the frequency domain, and based on this analysis, determining the presence and depth of the physiological event in the anatomical structure.

20. The optical measurement system of claim 1, wherein the optical detector is configured for sequentially detecting the first plurality of frequency components in the interference light, and wherein the processor is configured for analyzing the electrical signal in the time domain, and based on this analysis, determining the presence and depth of the physiological event in the anatomical structure.

21. The optical measurement system of claim 20, wherein the optical detector is a conventional camera, and the optical measurement system further comprises:

an optical modulator configured for intensity modulating the pump source light at a modulation frequency to create the pump sample light; and a controller that sequentially varies the modulation frequency, such that wherein multiple ones of the first plurality of frequency components are sequentially detected by the conventional camera.

22. The optical measurement system of claim 20, wherein the camera is a lock-in camera configured for sequentially locking into multiple ones of the first plurality of frequency components in the interference light.

23. The optical measurement system of claim 1, wherein the exiting sample light comprises multiple optical modes.

24. The optical measurement system of claim 1, wherein the interferometer comprises a beam splitter configured for splitting the probe source light into the probe sample light and the probe reference light, and an optical beam combiner configured for combining the signal light of the exiting sample light and the reference light into the interference light.

25. The optical measurement system of claim 1, wherein the processor is configured for determining the presence and depth of the physiological event in the anatomical structure by comparing the first plurality of frequency components in the electrical signal to a plurality of reference frequency components.

26. The optical measurement system of claim 1, wherein the pump optical source comprises a pump laser, and the probe optical source comprises a probe laser.

* * * * *